United States Patent
Vleugels

(10) Patent No.: US 12,217,194 B2
(45) Date of Patent: Feb. 4, 2025

(54) NUTRITIONAL CONTENT DETERMINATION BASED ON GESTURE DETECTION DATA

(71) Applicant: MEDTRONIC MINIMED, INC., Northridge, CA (US)

(72) Inventor: Katelijn Vleugels, Austin, TX (US)

(73) Assignee: Medtronic MiniMed, Inc., Northridge (CA)

( * ) Notice: Subject to any disclaimer, the term of this patent is extended or adjusted under 35 U.S.C. 154(b) by 0 days.

(21) Appl. No.: 18/322,318

(22) Filed: May 23, 2023

(65) Prior Publication Data

US 2023/0297858 A1    Sep. 21, 2023

Related U.S. Application Data

(63) Continuation of application No. 16/261,559, filed on Jan. 29, 2019, now abandoned, which is a continuation-in-part of application No. 15/835,361, filed on Dec. 7, 2017, now Pat. No. 10,790,054, and a continuation-in-part of application No. 15/419,996, filed on Jan. 30, 2017, now Pat. No. 10,373,716.

(Continued)

(51) Int. Cl.
| | |
|---|---|
| G16H 10/60 | (2018.01) |
| G06N 5/04 | (2023.01) |
| G06N 20/00 | (2019.01) |
| G16H 20/17 | (2018.01) |
| H04W 4/80 | (2018.01) |

(52) U.S. Cl.
CPC ............ G06N 5/04 (2013.01); G06N 20/00 (2019.01); G16H 10/60 (2018.01); G16H 20/17 (2018.01); H04W 4/80 (2018.02)

(58) Field of Classification Search
CPC .................................................. G06F 19/328
See application file for complete search history.

(56) References Cited

U.S. PATENT DOCUMENTS

| | | | |
|---|---|---|---|
| 4,562,751 | A | 1/1986 | Nason et al. |
| 4,685,903 | A | 8/1987 | Cable et al. |

(Continued)

FOREIGN PATENT DOCUMENTS

| | | | |
|---|---|---|---|
| CN | 101326526 A | 12/2008 | |
| CN | 102281817 A | 12/2011 | |

(Continued)

OTHER PUBLICATIONS

Amft, O. et al., "On-Body Sensing Solutions for Automatic Dietary Monitoring", IEEE Pervasive Computing, Apr. 2009, vol. 8, No. 2, pp. 62-70.

(Continued)

*Primary Examiner* — Di Xiao
(74) *Attorney, Agent, or Firm* — Weaver Austin Villeneuve & Sampson LLP

(57) ABSTRACT

Techniques disclosed herein relate to nutritional content determination based on gesture detection data. In some embodiments, the techniques involve obtaining gesture detection data corresponding to consumption of a food item or a drink; determining, based on the gesture detection data, nutritional content of the food item or the drink; and causing delivery of insulin in accordance with the nutritional content of the food item or the drink.

20 Claims, 9 Drawing Sheets

Related U.S. Application Data

(60) Provisional application No. 62/753,819, filed on Oct. 31, 2018, provisional application No. 62/623,418, filed on Jan. 29, 2018, provisional application No. 62/431,330, filed on Dec. 7, 2016, provisional application No. 62/288,408, filed on Jan. 28, 2016.

(56) References Cited

U.S. PATENT DOCUMENTS

| | | |
|---|---|---|
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Vanantwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,391,104 B2 | 3/2013 | De La Huerga |
| 8,771,251 B2 | 7/2014 | Ruchti et al. |
| 9,042,596 B2 | 5/2015 | Connor |
| 9,110,510 B2 | 8/2015 | Moore et al. |
| 9,254,099 B2 | 2/2016 | Connor |
| 9,317,916 B1 | 4/2016 | Hanina et al. |
| 9,396,369 B1 | 7/2016 | Whitehurst et al. |
| 9,442,100 B2 | 9/2016 | Connor |
| 9,529,385 B2 | 12/2016 | Connor |
| 9,536,449 B2 | 1/2017 | Connor |
| 9,640,088 B1 | 5/2017 | Whitehurst et al. |
| 9,672,328 B2 | 6/2017 | Saint et al. |
| 9,730,647 B2 * | 8/2017 | Eyring ............... A61B 5/486 |
| 10,102,342 B1 | 10/2018 | Vleugels et al. |
| 10,373,716 B2 | 8/2019 | Vleugels et al. |
| 10,790,054 B1 | 9/2020 | Vleugels et al. |
| 10,835,727 B2 | 11/2020 | Montalvo et al. |
| 10,950,052 B1 | 3/2021 | Shirley et al. |
| 11,069,443 B2 | 7/2021 | Vleugels et al. |
| 11,363,986 B2 | 6/2022 | Vleugels |
| 11,367,516 B2 | 6/2022 | Vleugels |
| 11,367,517 B2 | 6/2022 | Vleugels |
| 11,728,024 B2 | 8/2023 | Vleugels et al. |
| 11,759,399 B2 | 9/2023 | Vleugels |
| 11,929,167 B2 | 3/2024 | Vleugels et al. |
| 11,942,200 B2 | 3/2024 | Vleugels |
| 2002/0022774 A1 | 2/2002 | Karnieli |
| 2007/0123819 A1 | 5/2007 | Mernoe et al. |
| 2008/0027502 A1 | 1/2008 | Ransom |
| 2008/0234663 A1 * | 9/2008 | Yodfat ............... A61M 5/1723 604/890.1 |
| 2008/0267444 A1 | 10/2008 | Simons-Nikolova et al. |
| 2009/0012433 A1 | 1/2009 | Fernstrom et al. |
| 2009/0125825 A1 | 5/2009 | Rye et al. |
| 2009/0327171 A1 | 12/2009 | Tan et al. |
| 2010/0160861 A1 | 6/2010 | Causey, III et al. |
| 2010/0188328 A1 | 7/2010 | Dodge et al. |
| 2010/0194573 A1 | 8/2010 | Hoover et al. |
| 2011/0022224 A1 | 1/2011 | Park |
| 2011/0053122 A1 | 3/2011 | Hill et al. |
| 2013/0335418 A1 | 12/2013 | Kim et al. |
| 2014/0018636 A1 | 1/2014 | Contant et al. |
| 2014/0347491 A1 | 11/2014 | Connor |
| 2014/0349256 A1 | 11/2014 | Connor |
| 2014/0349257 A1 | 11/2014 | Connor |
| 2014/0377724 A1 | 12/2014 | Hoover et al. |
| 2015/0161558 A1 | 6/2015 | Gitchell et al. |
| 2015/0199484 A1 | 7/2015 | Morris et al. |
| 2015/0355716 A1 * | 12/2015 | Balasubramanian ....................... G06F 3/04186 345/173 |
| 2015/0379238 A1 | 12/2015 | Connor |
| 2016/0012749 A1 | 1/2016 | Connor |
| 2016/0026767 A1 | 1/2016 | Sarrafzadeh et al. |
| 2016/0030683 A1 | 2/2016 | Taylor et al. |

(56) References Cited

U.S. PATENT DOCUMENTS

| | | | |
|---|---|---|---|
| 2016/0073953 A1 | 3/2016 | Sazonov | |
| 2016/0112684 A1* | 4/2016 | Connor | G16H 20/60 |
| | | | 356/402 |
| 2016/0132642 A1 | 5/2016 | Carmi | |
| 2016/0163037 A1 | 6/2016 | Dehais et al. | |
| 2016/0232811 A9 | 8/2016 | Connor | |
| 2016/0260352 A1* | 9/2016 | Ortiz | G09B 19/00 |
| 2016/0283783 A1 | 9/2016 | Yang et al. | |
| 2016/0320850 A1 | 11/2016 | Thadani et al. | |
| 2016/0350514 A1* | 12/2016 | Rajendran | G06Q 10/10 |
| 2017/0039045 A1 | 2/2017 | Abrahami et al. | |
| 2017/0046568 A1 | 2/2017 | Bulzacki | |
| 2017/0173261 A1 | 6/2017 | O'Connor et al. | |
| 2017/0213014 A1 | 7/2017 | Su | |
| 2017/0220751 A1 | 8/2017 | Davis et al. | |
| 2017/0220772 A1 | 8/2017 | Vleugels et al. | |
| 2017/0262064 A1 | 9/2017 | Ofir et al. | |
| 2017/0357849 A1* | 12/2017 | Katsu | G06F 3/0346 |
| 2018/0028126 A1 | 2/2018 | Eyring | |
| 2018/0039765 A1 | 2/2018 | Ekambaram et al. | |
| 2018/0137251 A1* | 5/2018 | Pillalamarri | G16H 40/63 |
| 2018/0144104 A1 | 5/2018 | DiCristina et al. | |
| 2018/0169334 A1 | 6/2018 | Grosman et al. | |
| 2018/0174675 A1 | 6/2018 | Roy et al. | |
| 2018/0244908 A1 | 8/2018 | Sazonov et al. | |
| 2018/0292910 A1 | 10/2018 | Valafar et al. | |
| 2018/0353698 A1 | 12/2018 | Saint et al. | |
| 2018/0357388 A1 | 12/2018 | Nackaerts | |
| 2019/0000382 A1 | 1/2019 | Fitzpatrick | |
| 2019/0015596 A1 | 1/2019 | Saint et al. | |
| 2019/0168125 A1 | 6/2019 | Haile et al. | |
| 2019/0236465 A1 | 8/2019 | Vleugels | |
| 2020/0118665 A1 | 4/2020 | Bender et al. | |
| 2020/0135320 A1 | 4/2020 | Vleugels | |
| 2020/0289373 A1 | 9/2020 | Vleugels | |
| 2020/0294645 A1 | 9/2020 | Vleugels | |
| 2020/0327973 A1 | 10/2020 | Pryor et al. | |
| 2020/0357503 A1 | 11/2020 | Sugaya et al. | |
| 2020/0381101 A1 | 12/2020 | Vleugels et al. | |
| 2021/0178067 A1 | 6/2021 | Grosman et al. | |
| 2021/0178068 A1 | 6/2021 | Miller et al. | |
| 2021/0350920 A1 | 11/2021 | Vleugels et al. | |
| 2022/0301679 A1 | 9/2022 | Vleugels | |
| 2022/0378659 A1 | 12/2022 | Vleugels | |
| 2023/0335254 A1 | 10/2023 | Vleugels et al. | |
| 2023/0368046 A9 | 11/2023 | Vleugels | |
| 2024/0170145 A1 | 5/2024 | Vleugels et al. | |
| 2024/0185977 A1 | 6/2024 | Vleugels | |

FOREIGN PATENT DOCUMENTS

| | | | | |
|---|---|---|---|---|
| CN | 109863559 A | * | 6/2019 | G06F 19/3456 |
| CN | 113035322 A | | 6/2021 | |
| CN | 115039183 A | | 9/2022 | |
| EP | 4073813 A1 | | 10/2022 | |
| JP | 2004024699 A | | 1/2004 | |
| JP | 2012235869 A | | 12/2012 | |
| JP | 2017127653 A | | 7/2017 | |
| WO | 2018033513 A1 | | 2/2018 | |
| WO | 2020092573 A1 | | 5/2020 | |
| WO | 2021086741 A1 | | 5/2021 | |
| WO | 2021119541 A1 | | 6/2021 | |

OTHER PUBLICATIONS

European Office Action dated Jun. 3, 2022 in Application No. EP17745101.0.
International Preliminary Report on Patentability dated May 12, 2022, in PCT Application No. PCT/US2020/056959.
International Search Report and Written Opinion dated Apr. 10, 2017, International Patent Application No. PCT/US2017/015682, filed Jan. 30, 2017, 15 pages.
International Search Report and Written Opinion dated Feb. 15, 2021, in Application No. PCT/US2020/056959.
International Search Report and Written Opinion dated Mar. 18, 2021, in Application No. PCT/US2020/064693.
JP Office Action dated Oct. 3, 2023 in Application No. JP2021-523284 with English Translation.
Ogden, C. L. et al., "Prevalence of Childhood and Adult Obesity in the United States, 2011-2012", JAMA, Feb. 26, 2014, vol. 311, No. 8, pp. 806-814.
Oliver, A. et al.,"On-Body Sensing Solutions for Automatic Dietary Monitoring, Wearable Computing and Healthcare", IEEE Pervasive Computing, Apr.-Jun. 2007, vol. 8, No. 2, pp. 62-70.
Petersen, K. et al., "A New Software for Initiating and Optimising Insulin Treatment of Out-Patients", Computer Methods and Programs in Biomedicine, Department of Endocrinology, University Hospital of Internal Medicine, Freiburg, F.R.G., 1990, vol. 32, pp. 325-331.
Srisuphab, A. et al., "Artificial Neural Networks for Gesture Classification With Inertial Motion Sensing Armbands", IEEE Region 10 Conference TENCON, Nov. 2016, pp. 1-5.
U.S. Advisory Action dated Jul. 7, 2023, in U.S. Appl. No. 17/836,302.
U.S. Final Office Action dated Apr. 7, 2022 in U.S. Appl. No. 16/667,650.
U.S. Final office Action dated Apr. 26, 2023 in U.S. Appl. No. 17/836,302.
U.S. Final Office Action dated Feb. 24, 2023 in U.S. Appl. No. 16/261,559.
U.S. Non Final Office Action dated Oct. 28, 2021 in U.S. Appl. No. 16/886,353.
U.S. Non Final Office Action dated Oct. 28, 2021 in U.S. Appl. No. 16/886,329.
U.S. Non-Final Office Action dated Aug. 2, 2023, in U.S. Appl. No. 17/836,302.
U.S. Non-Final Office Action dated Dec. 8, 2022 in U.S. Appl. No. 17/886,293.
U.S Non-Final Office Action dated Feb. 1, 2022, in U.S. Appl. No. 16/886,360.
U.S. Non-Final office Action dated Jan. 12, 2023 in U.S. Appl. No. 16/999,005.
U.S. Non-Final Office Action dated Jul. 20, 2023, in U.S. Appl. No. 17/379,841.
U.S Non-Final Office Action dated May 16, 2022, in U.S. Appl. No. 16/886,360.
U.S. Non-Final office Action dated Nov. 22, 2022 in U.S. Appl. No. 17/836,302.
U.S. Non-Final Office Action dated Sep. 1, 2022 in U.S. Appl. No. 16/261,559.
U.S Non-Final Office Action dated Sep. 28, 2021, in U.S. Appl. No. 16/667,650.
Vu, T. et al., "Wearable Food Intake Monitoring Technologies: A Comprehensive Review", MDPI Journal, Computers, 2017, vol. 6, No. 4, pp. 1-28.
CA Office Action dated Feb. 13, 2023, in Application No. CA3013053.
CN Office Action dated Apr. 28, 2024 in CN Application No. 201980067166.6 with English translation.
International Preliminary Report on Patentability dated Aug. 9, 2018, in Application No. PCT/US2017/015682.
U.S. Non-Final Office Action dated Apr. 24, 2024 in U.S. Appl. No. 18/339,044.
U.S. Notice of Allowance dated Feb. 12, 2024 in U.S. Appl. No. 17/379,841.
U.S. Notice of Allowance dated Mar. 10, 2022 in U.S. Appl. No. 16/886,329.
U.S. Notice of Allowance dated Mar. 10, 2022 in U.S. Appl. No. 16/886,353.
U.S. Notice of Allowance dated Mar. 22, 2023 in U.S. Appl. No. 16/999,005.
U.S. Notice of Allowance dated May 3, 2023 in U.S. Appl. No. 17/886,293.
U.S. Notice of Allowance dated Nov. 22, 2023 in U.S. Appl. No. 17/836,302.
U.S. Notice of Allowance dated Oct. 3, 2023, in U.S. Appl. No. 16/261,559.

(56) References Cited

OTHER PUBLICATIONS

U.S. Notice of Allowance dated Oct. 26, 2023 in U.S. Appl. No. 17/379,841.
U.S Restriction requirement dated May 18, 2022 in U.S. Appl. No. 16/261,559.
CN Office Action dated Aug. 22, 2024 in CN Application No. 202110369826.5 with English translation.
U.S. Final Office Action dated Aug. 28, 2024 in U.S. Appl. No. 18/339,044.
U.S. Non-Final Office Action dated Sep. 6, 2024 in U.S. Appl. No. 18/443,888.

* cited by examiner

NUTRITIONAL CONTENT DETERMINATION BASED ON GESTURE DETECTION DATA

CROSS-REFERENCES TO RELATED APPLICATIONS

This application is a continuation of U.S. patent application Ser. No. 16/261,559, filed Jan. 29, 2019, which claims the benefit of U.S. Provisional Patent Application 62/623,418, filed Jan. 29, 2018, entitled "Activation of Ancillary Sensor Systems Based on Triggers from a Wearable Gesture Sensing Device."

U.S. patent application Ser. No. 16/261,559 also claims the benefit of U.S. Provisional Patent Application 62/753,819, filed Oct. 31, 2018, entitled "Automated Detecting of a Triggering Event and Signaling to a Medication Dispensing System or Messaging to a Patient or Caregiver."

U.S. patent application Ser. No. 16/261,559 further claims priority from U.S. patent application Ser. No. 15/419,996, filed Jan. 30, 2017, entitled "Method and Apparatus for Tracking of Food Intake and Other Behaviors and Providing Relevant Feedback" ("Vleugels I"), and U.S. patent application Ser. No. 15/835,361 filed Dec. 7, 2017, entitled "Method and Apparatus for Tracking of Food Intake and Other Behaviors and Providing Relevant Feedback" ("Vleugels II"). Vleugels I in turn claims the benefit of U.S. Provisional Patent Application 62/288,408, filed Jan. 28, 2016, entitled "Method and Apparatus for Food Intake Tracking and Feedback." Vleugels II in turn claims the benefit of U.S. Provisional Patent Application 62/431,330, filed Dec. 7, 2016, entitled "Machine Classification of Temporally-Limited Gesture Inputs."

Each of the above-cited applications or patents is hereby incorporated by reference in its entirety, as if set forth in full in this document, for all purposes.

FIELD OF THE INVENTION

The present invention relates generally to the medical arts and more particularly to nutritional content determination based on gesture detection data.

BACKGROUND

Gesture-sensing technology can be used to automatically detect a gesture event without user prompting or interaction, such as gestures to indicate events when someone is eating or drinking from their hand gestures using motion sensors (accelerometer/gyroscope) in a wristworn wearable device or ring. This detection can occur in real time to deduce key insights about the consumption activity such as, for example, a start time of a consumption event, an end time of the consumption event, a consumption method, metrics associated with pace of consumption, metrics associated with quantities consumed, and metrics associated with frequency of consumption, location of consumption, etc. The gesture-sensing technology can be used for other activities and behaviors such as smoking, dental hygiene, hand hygiene, etc. Examples are described in Vleugels I and Vleugels II.

Tracking food and nutrition intake can be error-prone, incomplete, tedious and disruptive. Even when gestures are sensed, it might require considerable user involvement and interruption to then manually process the sensed information, such as by logging. Software installed on or accessed from a tablet, mobile phone, laptop or computer, could facilitate logging and tracking of a person's food intake, but often that requires user intervention.

Specialty devices, such as tableware and utensils with built-in sensors have been proposed to track food intake more automatically. For example, a plate with integrated sensors and circuitry might automatically quantify and track the content of food that is placed on the plate. Similarly, integrated sensors in a drinking vessel might identify, quantify and track the contents of liquid in the cup. In another example, an eating utensil includes sensors that count the number of bites taken by a person using the eating utensil. These methods might fall short in not being able to automatically identify and quantify the content of the food being consumed and also only apply to a limited set of meal scenarios and dining settings and are not well suited to properly cover the wide range of different meal scenarios and dining settings that a typical person may encounter during a day. Additionally, these are not typically configured to integrate with electronic data from external sensing systems.

Being able to handle a wide variety of meal scenarios and settings is important for seamless and comprehensive food intake tracking. A method based on an eating utensil may not be able to properly track the intake of drinks, snacks or finger foods and such methods may also interfere with a person's normal social behavior. For example, it might not be socially acceptable for a user to bring their own eating utensils to a restaurant or a dinner at a friend's house.

Devices and methods have been described that quantify and track food intake based on analysis of images of food taken by a portable device that has imaging capabilities, such as an app that runs on a mobile phone or tablet that has a camera. Some devices might use spectroscopy to identify food items based on their molecular makeup. Such devices may use crowd sourcing and/or computer vision techniques, sometimes complemented with other image processing techniques, to identify a food item, estimate its nutritional content and/or estimate its portion size. However, many of these devices and methods are fond lacking in usability and availability in certain social settings.

Improved methods and apparatus for advanced gesture and event monitoring and analysis are needed.

SUMMARY

Techniques disclosed herein relate generally to providing guidance for configuring a medical device to a user in response to detected gestures of the user. The techniques may be practiced using a system comprising one or more processors and one or more processor-readable media; a processor-implemented method; and/or one or more non-transitory processor-readable media.

According to certain embodiments, the techniques involve obtaining gesture detection data corresponding to consumption of a food item or a drink; determining, based on the gesture detection data, nutritional content of the food item or the drink; and causing delivery of insulin in accordance with the nutritional content of the food item or the drink. In some embodiments, the techniques may also involve obtaining location information and/or time of event information corresponding to consumption of the food item or the drink.

In some embodiments, the gesture detection data may include consumption mode data indicating which utensils or equipment were used during consumption of the food item or the drink. In some embodiments, the gesture detection data may include consumption mode data indicating that utensils were not used during consumption of the food item. In some embodiments, the gesture detection data may include pace metrics for consumption of the food item or the drink. In some embodiments, the gesture detection data may include duration information for consumption of the food item or the drink.

The following detailed description together with the accompanying drawings will provide a better understanding of the nature and advantages of the present invention.

BRIEF DESCRIPTION OF THE DRAWINGS

Various embodiments in accordance with the present disclosure will be described with reference to the drawings, in which.

DETAILED DESCRIPTION

Figure 1:
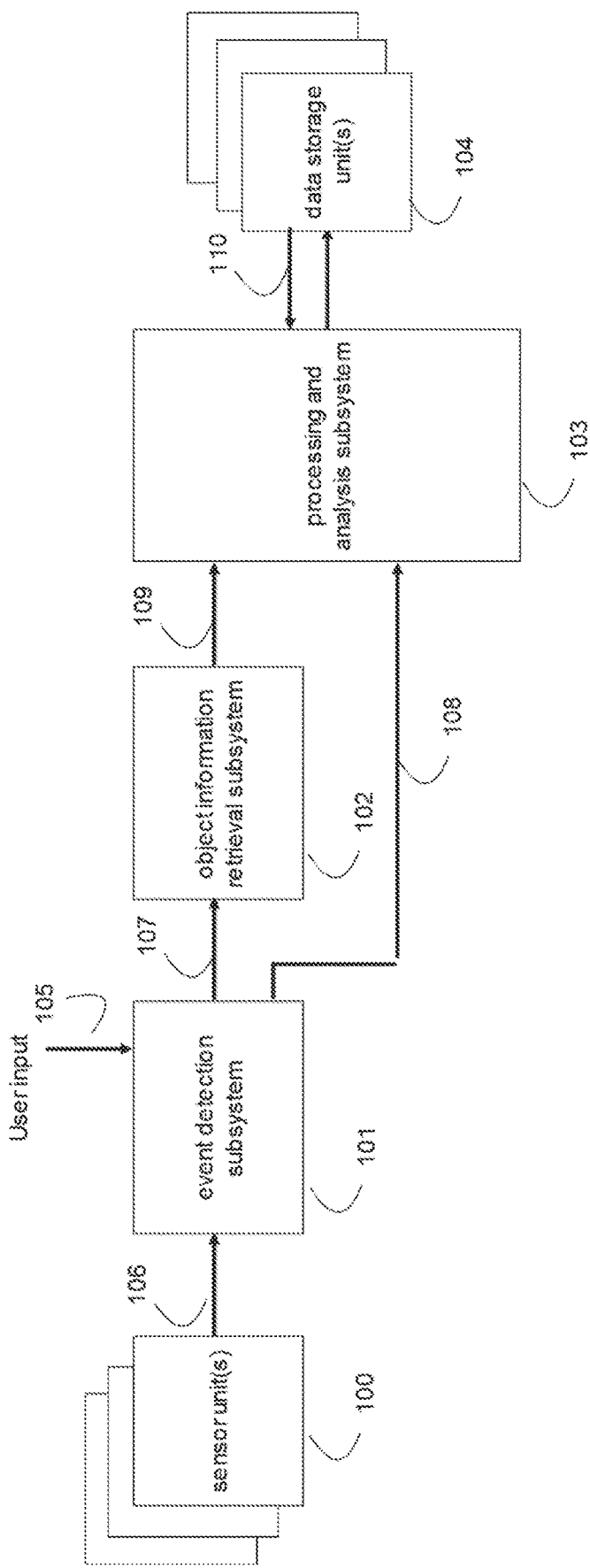
FIG. 1 illustrates an event monitoring system.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Various examples are provided herein of devices that a person would use to monitor, track, analyze and provide feedback on food intake, the intake process and timing and other relevant aspects of a person's eating, drinking and other consumption for various ends, such as providing diet information and feedback. The data related to food intake process might include, timing of the eating process, pace of eating, time since last food intake event, what is eaten, estimates of the contents of what is eaten, etc.

While many of the examples described herein are related to food intake events, the methods and devices described herein are also applicable to other behavior events such as brushing teeth, flossing, smoking, biting nails, taking medication, hand washing, putting on lipstick or mascara, shaving, making coffee, cooking, urinating, using the bathroom, driving, exercising or engaging in a specific sports activity. Other examples of an event that may be detected by an event detection subsystem could include an operator on a production line or elsewhere performing a specific task or executing a specific procedure. Yet another example could be a robot or robotic arm performing a specific task or executing a specific procedure on a production arm or elsewhere.

In some instances, it can be useful to also track information about objects or other subjects with which the subject interacts as they engage in an activity or exhibits certain behaviors. As an example, when a user is eating, it may be useful to not only detect and track that a user is eating, but to also detect and/or track information about what the user is eating. For example, it can be useful to know the brand, nutritional content or other information about the food being consumed. Likewise, when a user is drinking, it may also be useful to know the brand and content of the drink being consumed. When a user is brushing his teeth, it may be useful to know the brand of the toothpaste, or when a user is smoking it may be useful to also know the brand, type of product being lightened or nicotine content. When a user takes a pill, it may be useful to know what medication the user is taking and the dosage. It may not always be possible to derive this level of detail about the objects from analyzing just the hand gestures of a user or by simply processing the signals that are used to determine the onset or occurrence of an event or behavior, but with the additional information provided by the ancillary sensor systems, this information can be obtained and used or stored with records of the inferred events.

Data can be obtained from some stationary device having sensors and electronics, some mobile device having sensors and electronics that is easily moved and carried around by a person, and/or from wearable devices having sensors and electronics that a person attaches to their person or clothing, or is part of the person's clothing. In general, herein such devices are referred to as sensing devices. The data might be raw sensor data provided by the sensors capable of outputting data, or the data might be processed, sampled, or organized in some way so as to be data derived from the outputs of sensors.

Herein, the person having such a device and who's consumption is being monitored is referred to as the user but it should be understood that the device might be used unchanged in situations where the person consuming, the person monitoring, and the person evaluating feedback need not all be the same person. Herein, what is consumed is referred to as food intake, but it should be clear that these devices can be used to more generally track consumption and consumption patterns. A behavior tracking/feedback system as described herein might comprise one or more wearable devices and might also comprise one or more additional devices that are not worn. These additional devices might be carried by the wearer or kept nearby so that they can communicate with the wearable devices. The behavior tracking/feedback system might also comprise remote elements, such as a remote cloud computing element and/or remote storage for user information.

A wearable device might be worn at different locations on the wearer's body (i.e., the person monitoring their behavior) and the wearable device might be programmed or configured to account for those differences, as well as differences from wearer to wearer. For example, a right-handed person may wear the device around his right wrist whereas a left-handed person may wear the device around his left wrist. Users may also have different preferences for orientation. For example, some users may want the control buttons on one side, whereas other users may prefer the control buttons on the opposite side. In one embodiment, the user may manually enter the wrist preference and/or device orientation.

In some embodiments, sensing devices can sense, without requiring user interaction, the start/end of a food intake event, the pace of eating, the pace of drinking, the number of bites, the number of sips, the estimation of fluid intake, and/or estimation of portion sizing. Operating with less human intervention, no human intervention, or only intervention not apparent to others will allow the devices to scale well with different meal scenarios and different social situations. Sensing might include capturing details of the food before it is consumed, as well as user actions that are known to accompany eating, such as repeated rotation of an upper arm or other hand-to-mouth motions. Sensors might include an accelerometer, a gyroscope, a camera, and other sensors.

Using the devices can provide a person with low friction-of-use to detect, quantify, track and provide feedback related to the person's food intake content as well as the person's food intake behavior. Such methods have the potential of preventing, treating and, in certain cases, even curing diet-related diseases. Such devices can improve efficacy, accuracy and compliance, and reduce the burden of usage and to improve social acceptance. The devices can operate autonomously with no, or very minimal, human intervention, and do not interfere in an invasive or otherwise significant negative way with a person's normal activities or social interactions or intrude on the person's privacy. The devices are able to handle a wide range of meal scenarios and dining settings in a discreet and socially-acceptable manner, and are capable of estimating and tracking food intake content and quantity as well as other aspects of eating behavior. The devices can provide both real-time and non-real-time feedback to the person about their eating behavior, habits and patterns.

The devices might be useful for a person concerned about their diet. For example, people with Type 1 diabetes are usually on an insulin therapy where, based on their food intake and other factors, they administer the proper insulin dosage. While the cause of Type 1 diabetes may not be directly linked to a person's eating behavior, a person with Type 1 diabetes needs to carefully track his or her food intake in order to manage his or her insulin therapy. Such patients will also benefit from easier to use and more discreet methods for food intake tracking. In some embodiments of the sensing devices, the sensing device is part of a feedback-driven automated insulin delivery therapy system. Such a system might include one or more of continuous monitoring of a patient's glucose levels, a precision insulin delivery system, and the use of insulin that has a faster absorption rate, that would further benefit from information that can be extracted from automated and seamless food intake tracking, such as the tracking of carbohydrates and sugar intake. The devices might also be useful for wellness programs and the like.

A food intake event generally relates to a situation, circumstance or action whereby a person eats, drinks or otherwise takes into his or her body an edible substance. Edible substances may include, but are not limited to, solid foods, liquids, soups, drinks, snacks, medications, vitamins, drugs, herbal supplements, finger foods, prepared foods, raw foods, meals, appetizers, main entrees, desserts, candy, breakfast, sports or energy drinks. Edible substances include, but are not limited to, substances that may contain toxins, allergens, viruses, bacteria or other components that may be harmful to the person, or harmful to a population or a subset of a population. Herein, for readability, food is used as an example of an edible substance, but it should be understood that other edible substance might be used instead of food unless otherwise indicated.

Eating habits and patterns generally relate to how people consume food. Eating habits and patterns may include, but are not limited to, the pace of eating or drinking, the size of bites, the amount of chewing prior to swallowing, the speed of chewing, the frequency of food intake events, the amount of food consumed during a food intake event, the position of the body during a food intake event, possible movements of the body or of specific body parts during the food intake event, the state of the mind or body during a food intake event, and the utensils or other devices used to present, handle or consume the food. The pace of eating or drinking might be reflected in the time between subsequent bites or sips.

Triggers generally relate to the reasons behind the occurrence of a food intake event, behind the amount consumed and behind how it is consumed. Triggers for food intake events and for eating habits or patterns may include, but are not limited to, hunger, stress, social pressure, fatigue, addiction, discomfort, medical need, physical location, social context or circumstances, odors, memories or physical activity. A trigger may coincide with the food intake event for which it is a trigger. Alternatively, a trigger may occur outside the food intake event window, and might occur prior to or after the food intake event at a time that may or may not be directly related to the time of the food intake event.

In some embodiments of the sensing device or system, fewer than all of the features and functionality presented in this disclosure are implemented. For example, some embodiments may focus solely on detection and/or processing and tracking of the intake of food without intending to steer the user to modify his or her food intake or without tracking, processing or steering eating habits or patterns.

In many examples herein, the setting is that an electronic device is provided to a user, who wears the electronic device, alone or while it is in communication with a nearby support device that might or might not be worn, such as a smartphone for performing operations that the worn electronic device offloads. In such examples, there is a person wearing the electronic device and that person is referred to as the "wearer" in the examples and the system comprises a worn device and may include other components that are not worn and are nearby and components that are remote, preferably able to communicate with the worn device. Thus, the wearer wears the electronic device, and the electronic device includes sensors, which sense environment about the wearer. That sensing can be of ambient characteristics, body characteristics, movement and other sensed signals as described elsewhere herein.

In many examples, functionality of the electronic device might be implemented by hardware circuitry, or by program instructions that are executed by a processor in the electronic device, or a combination. Where it is indicated that a processor does something, it may be that the processor does that thing as a consequence of executing instructions read from an instruction memory wherein the instructions provide for performing that thing. While other people might be involved, a common example here is where the wearer of the electronic device is using that electronic device to monitor their own actions, such as gestures, behavior events comprising a sequence of gestures, activities, starts of activities or behavior events, stops of activities or behavior events, etc. Where it is described that a processor performs a particular process, it may be that part of that process is done separate from the worn electronic device, in a distributed processing fashion. Thus, a description of a process performed by a processor of the electronic device need not be limited to a processor within the worn electronic device, but perhaps a processor in a support device that is in communication with the worn electronic device.

FIG. 1 shows a high level functional diagram of a monitoring system of a subject in accordance with an embodiment of the present invention. As shown in FIG. 1, sensor units 100 interact with an event detection system 101, that in turn interacts with an object information retrieval system 102, that provide inputs to a processing and analysis system 103, the results of which can be stored in data storage units 104.

Other variants are also possible. For example, object information retrieval system 102 may provide inputs back to event detection system 101 that in turn forward inputs to processing and analysis system 103. Other variants of how the data gets processed and stored in data storage unit 104 are also possible.

In some embodiments, elements shown in FIG. 1 are implemented in electronic hardware, while in others some elements are implemented in software and executed by a processor. Some functions might share hardware and processor/memory resources and some functions might be distributed. Functionality might be fully implemented in a sensor device such as wrist worn wearable device, or functionality might be implemented across the sensor device, a processing system that the sensor device communicates with, such as a smartphone, and/or a server system that handles some functionality remote from the sensor device. For example, a wearable sensor device might make measurements and communicate them to a mobile device, which may process the data received from the wearable sensor device and use that information possibly combined with other data inputs, to activate object information retrieval subsystem 102. Object information retrieval subsystem 102 may be implemented on the mobile device, on the wearable sensor device, or on another electronic device. The object information retrieval subsystem 102 may also be distributed across multiple devices such as for example across the mobile device and the wearable sensor device. Data or other information may be stored in a suitable format, distributed over multiple locations or centrally stored, in the form recorded, or after some level of processing. Data may be stored temporarily or permanently. Data may be stored locally on the wearable sensor device, on the mobile device or may be uploaded over the Internet to a server.

Monitoring System Overview

A first component of the system illustrated in FIG. 1 is the event detection subsystem 101. One role of event detection subsystem 101 is to identify the actual, probable or imminent occurrence of an event. An event could, for example, be an event related to a specific activity or behavior. Specific activities or behaviors may include, but are not limited to, eating, drinking, smoking, taking medication, brushing teeth, flossing, hand washing, putting on lipstick or mascara, shaving, making coffee, cooking, urinating, using the bathroom, driving, exercising or engaging in a specific sports activity. Other examples of an event that may be detected by event detection subsystem 101 could be an operator on a production line or elsewhere performing a specific task or executing a specific procedure. Yet another example could be a robot or robotic arm performing a specific task or executing a specific procedure on a production arm or elsewhere.

The event detection subsystem may use inputs from one or more sensor units 100, other user inputs 105, or a combination of one or more sensor inputs from sensor unit 100 and one or more other user inputs 105 to determine or infer the actual, probable or imminent occurrence of an event. The event detection subsystem 101 may do additional processing on the sensor and/or user inputs to determine the actual, probable or imminent occurrence of an event. In general, the event detection system records and/or reacts to an inferred event, which occurs when the event detection system has inputs and/or data from which it determines that an event might actually be starting, might likely start, or is imminent. In some cases, the event detection system might infer an event where an event did not actually occur and process it as an event, but this might be an infrequent occurrence.

The event detection subsystem 101 may also do additional processing on the sensor and/or user inputs to determine additional information about the event. Such information may include, but is not limited to, the duration of the event, the event start time, the event end time, metrics associated with the speed or pace at which subject is engaging in the event. Other event data elements are also possible. For example, if the event is an eating event, an event data element could be the number of bites or the amount of food consumed. Similarly, if the event is a drinking event, an event data element could be the number of sips or the amount of fluid intake. These event data elements might be stored in a database that maintains data elements about inferred events.

Using the gesture sensing technology, an event detection system can trigger and external device to gather further information.

In a specific embodiment, the electronic device that houses object information retrieval subsystem 102 or a portion of object information retrieval subsystem 102 includes Near-Field-Communication (NFC) technology and the object information retrieval subsystem 102 obtains information about the object(s) or subject(s) with which the subject may be interacting at least in part via transmission over a wireless NFC link.

In a specific embodiment, the external device is a NFC reader and various objects having NFC tags thereon are detected. The NFC reader might be integrated with the gesture sensing technology or with some components of the gesture sensing technology.

Where those objects are food/beverage related, the event detection system can determine what the gestures are related to. For example, food/beverage containers might have NFC tags embedded in the product packaging and a food intake monitoring system might automatically determine that gestures are related to an eating event, then signal to an NFC reader to turn on and read nearby NFC tags, thereby reading the NFC tags on the products being consumed so that the gestures and the event are associated with a specific product.

In an example, a monitoring system might have a wearable device that determines gestures and based on those gestures, identifies an eating event or a drinking event. Suppose a drinking event is detected and based on the sensor inputs and gestures detected, the monitoring system determined that the user drank three quarters of a can of soda, such as be counting sips and estimating or computing the size of each sip. As the gestures are likely identical regardless of whether it is a diet soda or a regular soda. Using the NFC reader, the specific brand and type of soda can be detected as well.

The sensors may be in the wearable device, with gesture determination logic or processing occurring in an external device that is communicatively coupled to the wearable device, such as a mobile phone, or the gesture determination may partially happen on the wearable device and partially on the external device that is communicatively coupled to the wearable device.

The NFC reader may be in the wearable device that houses the sensors, in an external device that is communicatively coupled to the wearable device and that performs at least some of the gesture determination or in another external device that is communicatively coupled to the wearable device, to an external device that performs at least some of the gesture determination or to both.

In the general case, the detection of the occurrence of an event may be used to initiate a process/system/circuitry/device to collect information about objects/items or other subjects that are being interacted with by the person performing the activity or behavior represented by the event. This information may be recorded in the form of data elements. Object data elements may be stored in a database. One or more object data elements and one or more event data elements of the same event may be recorded as a single entry in a database. Object data elements and event data elements may also be recorded as separate entries in a database. Other data structures consistent with the teachings herein might also be used, or used instead.

When the NFC reader system gets activated, it initiates one or more NFC read commands, and additional information from relevant objects is obtained wirelessly over NFC link. Additional processing may be applied, such as filtering out the NFC data to simplify processing downstream.

In other variations, other wireless links are used instead of NFC or with NFC. Examples of other wireless technologies include but are not limited to Bluetooth, Bluetooth Low Energy, Wi-Fi, Wi-Fi derivatives, and proprietary wireless technologies.

The wireless module or device used by object information retrieval subsystem 102 may also be used for other purposes. For example, if the wireless module is a Bluetooth or Bluetooth Low Energy module, and the object information retrieval subsystem is housed inside a smartphone, the wireless module may also be used for wireless communication with other devices that are wirelessly connected to the smartphone, such as for example wireless earphones, a wireless continuous glucose monitoring device, a wireless entertainment system.

The wireless module may use a certain wireless communication protocol ("primary protocol"), such as Bluetooth or Bluetooth Low Energy to communicate with the other devices. When used by object retrieval information subsystem 102 to retrieve information from objects the wearer may be interacting with, the wireless module may use a modified wireless communication protocol ("secondary protocol") for example, to reduce power consumption of the objects it is retrieving information from. The secondary protocol may be partially, but not fully, compliant with the primary protocol. For example, the secondary protocol may only implement a subset of the functionality of the primary protocol, may have different limits on maximum packet size, may have longer time intervals between packet exchanges, may support only a subset of the supported data rates, may use modified frame formats. In general, a partially compliant secondary protocol is one where a device using the secondary protocol can communicate with other devices using the secondary protocol, and perhaps the primary protocol, where nearby devices that are using the primary protocol are able to process at least something about the secondary protocol communications, instead of perhaps treating them as noise or interference, but in some way the device using the secondary protocol is not fully compliant with the primary protocol. An example is low-power, or unpowered, Bluetooth tags that are able to communicate using parts of the Bluetooth protocol, but do not implement all of the required or expected features of the Bluetooth protocol.

As an example, a very low power tag might be powered solely by impinging electrical fields (like an NFC tag) and might be a tag that implements parts of the Bluetooth protocol, but not the more power-intensive parts, and can still communicate with a tag reader. It may be that an event detection system is agnostic to the type of tag reader, or it might specifically expect the tag reader to look for, and read, very low power tags. A wireless network protocol implemented by Bluetooth tag may support a subset of the protocol of the wireless module in the object retrieval information subsystem. This would allow the wireless module in the object retrieval information subsystem to operate as a regular Bluetooth/Bluetooth LE device, but it can also receive/decode frames sent by a lower-powered Bluetooth tag using a modified protocol with enough functionality implemented such that it can receive/decode packets received from the main wireless module. Thus, in a specific embodiment, the external device is a Bluetooth module or a Bluetooth Low Energy module and various objects having Bluetooth tags use energy scavenging as their sole or partial source of power and those tags can be detected. The Bluetooth module might be integrated with the gesture sensing technology or with some components of the gesture sensing technology. Other wireless network protocols are also possible.

The detection of occurrence of an event signal may be used to filter out information about specific, relevant objects that are related to the activity/behavior of interest that are part of the event.

While the object detection process might be automatic, it can also have user intervention required to activate the object information retrieval system. For example, it could be as simple as asking the user to turn on a camera, or make a decision whether to continue the detection process and get the user's input on the decision. As another example, the user may be prompted to move the NFC reader closer to the NFC tag of interest. In another example, the user may be prompted to activate the NFC reader circuitry, or portions of the NFC reader circuitry or take one or more actions that allow the NFC reader circuitry to issue read command.

In addition to an NFC reader, a camera might be activated and additional information from relevant objects is obtainable by analyzing images or video recording of relevant objects. The camera might be combined in a unit with the NFC reader. In some embodiments, only a camera is used, or other ancillary sensors are used to obtain additional information about the event.

Information about the activity or behavior that are part of the event, obtained from the event detection subsystem can be combined with information about the object(s) or subject(s) the user is interacting with, and additional processing/analysis may be performed on the combined dataset to obtain additional information or insights about the activity/behavior that cannot be obtained from looking at only one of the data sources alone.

While many examples in this disclosure refer to the event detection system analyzing gestures to detect the actual, likely or imminent occurrence of an event, other sensor inputs are also possible. For example, audio signals in or near the mouth, throat or chest may be used to detect and obtain information about a user's consumption. To accomplish this, the event detection subsystem 101 may use inputs 107 from one or more sensor units 100. Sensors may include, but are not limited to, accelerometers, gyroscopes, magnetometers, magnetic angular rate and gravity (MARG) sensors, image sensors, cameras, optical sensors, proximity sensors, pressure sensors, odor sensors, gas sensors, glucose sensors, heart rate sensors, ECG sensors, blood pressure sensors, thermometers, light meters, Global Positioning Systems (GPS), and microphones.

Methods for event detection may include, but are not limited to, detection based on monitoring of movement or position of the body or of specific parts of the body, monitoring of arm movement, position or gestures, monitoring of hand movement, position or gestures, monitoring of finger movement, position or gestures, monitoring of swallowing patterns, monitoring of mouth and lips movement, monitoring of saliva, monitoring of movement of cheeks or jaws, monitoring of biting or teeth grinding, monitoring of signals from the mouth, the throat and the digestive system. Methods for detection may include visual, audio or any other types of sensory monitoring of the person or robot/machine and/or his or her surroundings. Data analytics techniques, including but not limited to statistics, machine learning and artificial intelligence techniques may be applied to detect the actual, probably or imminent occurrence of an event.

Upon the detection of an actual, probable or imminent occurrence of an event, the event detection subsystem may activate the object information retrieval subsystem 102. Alternatively, the event detection subsystem 101 may do additional processing to decide whether or not to activate the object information retrieval subsystem 102. The event detection subsystem 101 may activate the object information retrieval subsystem 102 immediately or wait for a certain time before activating the object information retrieval subsystem 102.

The role of object information retrieval subsystem 102 is to collect information about objects or other subjects a subject is interacting with when or some time after the event detection subsystem 101 has detected the occurrence of an actual, probable or imminent event.

In one such embodiment, upon receiving an activation input signal 107 from event detection subsystem 101, or some time after receiving an activation input signal 107, object information retrieval subsystem 102 initiates an NFC read action to read the NFC tag attached to, housed within or otherwise associated with one or more objects that are within NFC range of the device that houses object information retrieval subsystem 102. Object information retrieval subsystem 102 sends the data received from one or more objects to processing and analysis subsystem 103. Object information retrieval subsystem 102 may do additional processing on the data before sending it to processing and analysis subsystem 103. In other embodiments, additional ancillary sensors or sensor systems might be used, such as a camera or other electronic device.

Processing may include but is not limited to filtering, extracting specific data elements, modifying data or data elements, combining data or data elements obtained from multiple objects, combing data or data elements with data obtained from other sources not collected via NFC. Examples of filtering may include but are not limited to filtering based on distance or estimated distance between the object or objects and object information retrieval subsystem, based on signal strength of received NFC signals, based on order in which data is received from objects, based on information in the data or in specific data elements. Other filtering mechanisms or criteria used for filtering are also possible. Object information retrieval subsystem 102 may stop reading NFC tags after a fixed time, after a configurable time, after reading a fixed or configurable number of tags. Other criteria may also be used.

It is also possible, that the object information retrieval subsystem collects information about objects or other subjects a subject is interacting with independent of the event detection subsystem. In such an embodiment, the processing and analysis subsystem 103 may use signals 108 received from event detection subsystem 101 with data signals 109 received from object information retrieval subsystem 102 to deduce relevant information about objects or other subjects a subject may be interacting during an activity or when exhibiting a certain behavior.

In a specific embodiment of this disclosure, object information retrieval subsystem 102 continuously, periodically or otherwise independently from inputs from event detection subsystem 101 reads NFC tags from object that are within range of the electronic device that houses object information retrieval subsystem 102 in its entirety or in part. The detection of occurrence of an activity/behavior signal may be used to filter out information about specific, relevant objects that are related to the activity/behavior of interest. Where the objects are associated with an event, indications of, or references to, the specific objects might be recorded as part of a record of the event, so that the information can be later used for filtering or other processing.

In a specific embodiment, object information retrieval subsystem 102 collects data independent from inputs it receives from the event detection subsystem but only sends data to processing and analysis subsystem 103 when or some time after, it receives an activation signal 107 from event detection subsystem 101. Object information retrieval subsystem 102 may send only a subset of the data it has received from objects over an NFC link. For example, it may only send data that it receives in a fixed or configurable time window related to the time it receives the activation signal 107. For example, it may only send data immediately preceding and/or immediately following the activation signal 107. Other time windows are also possible. Object information retrieval subsystem 102 may do additional processing on the data before sending it to processing and analysis subsystem 103.

In one embodiment of this disclosure, the object information retrieval subsystem 102 includes a camera and the information about the object or objects may be derived from the analysis of an image or video recording as described in detail in patent application Vleugels II.

In a preferred embodiment of this disclosure, object information retrieval subsystem 102 collects data from objects without any intervention or input from the subject. In another embodiment of this disclosure, some user input or intervention is required. For example, the user may be prompted to move the NFC reader closer to the NFC tag of interest. In another example, the user may be prompted to activate the NFC reader circuitry, or portions of the NFC reader circuitry or take one or more actions that allow the NFC reader circuitry to issue read command.

Figure 2:
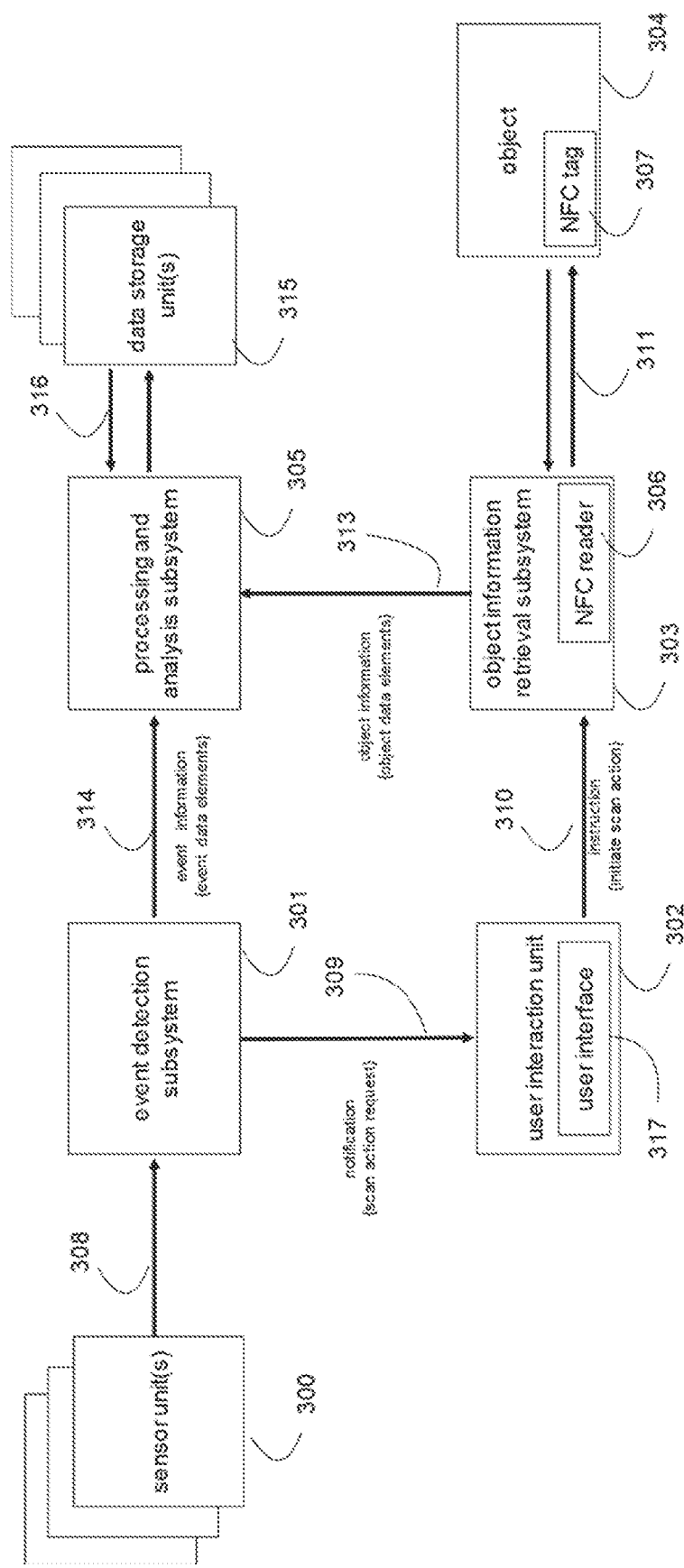
FIG. 2 illustrates a process to provide for user intervention.

FIG. 2 shows a high level functional diagram of a monitoring system in accordance with an embodiment of the present invention that requires user intervention. As shown in FIG. 2, one or more sensor units 300 interact with event detection subsystem 301 and send sensor data to event detection subsystem 301. Upon detection or inference of an actual, probable or imminent event, event detection subsystem sends one or more notifications to user interaction unit 302 to request activation of NFC scan action. Notifications may be rendered to the user as a displayed text message, as a displayed image, as an audio message, as a LED signal, as a vibration, etc. A combination of user interfaces may also be used. Other user interfaces may also be used. The user may respond to the notification(s) using one or more user interfaces of the user interaction unit 302. A user response may trigger user interaction unit 302 to send a scan command 310 to object information retrieval subsystem 303. Upon receiving scan command 310 or some time after receiving scan command 310, object information retrieval subsystem 303 may activate NFC reader 306 and obtain information about object 304 over a wireless communication link 311 between NFC reader 306 and NFC tag 307. Information obtained over wireless link 311 may contain information about brand, type, content, expiration date, lot number, etc., of object 304. Other information about the object may also be retrieved. Event data elements 314 from event detection subsystem 301 and object data elements 313 retrieved by object information retrieval subsystem 303 from one or more objects over a wireless link 311 may be sent to processing and analysis subsystem 305. Additional processing may be performed and the event and object data elements may be stored in a database on one or more data storage units 315.

In another example, the event detection system automatically scans for NFC tags, but upon receiving data from an object, the object information retrieval subsystem sends a message to the subject and the subject authorizes, or not, transmission to a processor or analysis subsystem or the subject confirms the information directly. This message may also be sent by processing and analysis subsystem.

Processing by processing and analysis subsystem 103 may include but is not limited to filtering, extracting specific data elements, modifying data or data elements, combining data or data elements obtained from multiple objects, combing data or data elements with data obtained from other sources not collected via NFC. Examples of filtering may include but are not limited to filtering based on distance or estimated distance between object or objects and object information retrieval subsystem, based on signal strength of received NFC signals, based on order in which data is received from objects, based on information in the data or in specific data elements. Other filtering mechanisms or criteria used for filtering are also possible. Object information retrieval subsystem 102 may stop sending data after a fixed time, after a configurable time, after reading a fixed or configurable number of tags. Other criteria may also be used. Object information retrieval subsystem 102 may send data only from a single object, from a subset of objects or from all objects for which it receives data within the specified time window.

In a different embodiment of this disclosure, object information retrieval subsystem 102 continuously, periodically or otherwise independently from inputs from event detection subsystem 101 reads NFC tags from object that are within range of the electronic device that houses object information retrieval subsystem 102 in its entirety or in part and sends such data to processing and analysis subsystem 103 independent of any signals from event detection subsystem.

Processing and analysis subsystem 103 receives data inputs from event detection subsystem 101 and object information retrieval subsystem 102. It is also possible that processing and analysis subsystem 103 receives inputs only from object information retrieval subsystem 102. Processing and analysis subsystem 103 may do additional processing on the data and analyze the data to extract information about the object(s) or subject(s) from the data it receives. Processing may include but is not limited to filtering, extracting specific data elements, modifying data or data elements, combining data or data elements obtained from multiple objects. Analysis may also include comparing specific data elements to data that is stored in a look up table or database, correlating data elements to data elements that were obtained at an earlier time and/or from different subjects. Other processing and analysis steps are also possible. Processing and analysis subsystem 103 may store raw or processed data in data storage unit(s) 104. Storage may be temporary or permanent.

In some embodiments, the outputs from processing and analysis subsystem 103 may be available in real-time, either during or shortly after the event. In other embodiments, the outputs may not be available until a later time.

Processing and analysis subsystem 103 may be implemented on the mobile device, on the wearable sensor device, or on another electronic device. Processing and analysis subsystem 103 may also be distributed across multiple devices such as for example across the mobile device and the wearable sensor device. In another example, processing and analysis subsystem 103 may be distributed across the mobile device and a local or remote server. Processing and analysis subsystem 103 may also all be implemented on a local or remote server. Information may be stored in a suitable format, distributed over multiple locations or centrally stored, in the form recorded, or after some level of processing. Data may be stored temporarily or permanently. Data may be stored locally on the wearable sensor device, on the mobile device or may be uploaded over the Internet to a server.

The object information retrieval subsystem may be housed in its entirety or in part inside a battery operated electronic device and it may be desirable to minimize the power consumption of the object information retrieval subsystem. When no event is detected, the radio circuitry (e.g., the NFC reader circuitry or Bluetooth Low Energy module) may be placed in a low power state. Upon detection or inference of an actual, probable or imminent occurrence of an event, the object information retrieval subsystem may be placed in a higher power state. One or more additional circuitry inside the object information retrieval subsystem may be powered up to activate the object information retrieval subsystem, to improve the range or performance of object information retrieval subsystem, etc. In one specific example, the NFC reader is disabled or placed in a low power standby or sleep mode when no event is detected. Upon detection or inference of an event, the NFC reader is placed in a higher power state in which it can communicate with NFC tags of neighboring objects. After reading a pre-configured number of NFC tags, after a pre-configured time or upon detection of the end or completion of the event, the NFC reader may be disabled again or may be placed back into a low power standby or sleep mode.

Application: Food Logging

In existing food journaling methods, if a user forgets to make an entry or does not make an entry for another reason (intentionally or unintentionally), there is no record or history of the eating event. This leads to food diaries being incomplete, inaccurate and considerably less useful for therapeutic purposes. Furthermore, content recorded in existing food logging methods is typically limited to self-reporting of content and amounts. There is no information about important characteristics of how the food was consumed (e.g., pace, duration of meal).

The monitoring system shown in FIG. 1 may be used to automate or reduce the friction of food logging. In one embodiment of the present disclosure, event detection subsystem 101 uses information deduced from motion sensors such as an accelerometer or gyroscope to detect and monitor eating or drinking events from a subject's hand gestures. In other embodiments, different sensor inputs may be used to deduce eating or drinking events. Other sensors may include, but are not limited to, heart rate sensors, pressure sensors, proximity sensors, glucose sensors, optical sensors, image sensors, cameras, light meters, thermometers, ECG sensors and microphones.

Outputs of event detection subsystem 101 that indicate the occurrence of a subject's eating or drinking events are recorded. Event detection subsystem 101 may do additional processing to obtain additional relevant information about the event such as start time, end time, metrics representative of the subject's pace of eating or drinking, metrics representative of quantities consumed. This additional information may also be recorded.

The detection of the occurrence of an eating or drinking event may be recorded as an entry in a food journal. Additional information associated with the eating or drinking event that can be obtained from the event detection subsystem may also be recorded as part of the consumption event entry in the food journal. This can take the place of manually entering each eating event. The information could be stored on a remote server, integrated in a mobile app and displayed to the user, or integrated with a user's personal medical record, or shared with a healthcare provider, insurer, caregiver or other entity or person who has an interest or reason to receive food journaling information. Information about eating or drinking events being recorded may include time of event, duration of event, location of event, metrics related to pace of consumption, metrics related to quantities consumed, eating method(s), utensils used, etc.

In another embodiment of the present disclosure, the detection of the actual, imminent or probably start of an eating or drinking event may trigger a camera module to be activated and information about the content of consumed foods and drinks may be obtained from image analysis as described in Vleugels I and/or Vleugels II.

In a variation, upon detection of an eating or drinking event, an object information retrieval subsystem may be activated to collect additional information about the content of the foods or drinks. In one embodiment of the current disclosure, upon detection of the occurrence of an eating or drinking event, an object information retrieval subsystem automatically activates an NFC reader and wirelessly obtains information about the brand, type and/or content of foods and/or drinks being consumed from NFC tags that are built into or attached to the packaging of foods and/or drinks being consumed. This can take the place of manually entering each eating event and what was eaten. This information is then added to the eating or drinking event records in the subject's food log. Other embodiments are also possible. Some user intervention may be required to activate the NFC reader. For example, the user may be prompted to move the NFC reader closer to the NFC tag of interest. In another example, the user may be prompted to activate the NFC reader circuitry, or portions of the NFC reader circuitry or take one or more actions that allow the NFC reader circuitry to issue read command.

Processing and analysis subsystem 103 may combine inputs received from event detection subsystem 101 and object information retrieval subsystem 102 to derive information about a subject's activity or behavior related to an event that cannot be derived from just one of the inputs alone. For example, the data obtained from object information retrieval subsystem 102 may provide information that the subject is eating a specific food, but may not provide any information how much of the food item is consumed or how fast the specific food item is consumed. The pace and quantity in turn may be derived from data received from event detection subsystem 101. By combining the information from both subsystem, it becomes possible to derive a more comprehensive and accurate model of a subject's actual activities and behaviors.

In a simple embodiment, information obtained from event detection subsystem may be used to automatically record eating and/or drinking events in a food journal. Additional information about the eating or drinking event such as start time, end time, duration, pace, and quantities consumed may also be recorded. In one example, the user may still have to enter the content of the foods or drinks consumed manually, but the food log uploading would provide an entry which the user can complete. In other variations, the multiple sources could be merged or combined in other ways.

In another example, additional processing may be performed whereby the recorded information of an eating event is compared to the information from previous eating events. The comparison against historical information is used to determine or predict what the subject is eating. As one example, at one point in time, the content of the food(s) being consumed is added to the food journal. This may be a manual entry by a user, may be based on the analysis of an image of the food, may be based on information obtained from the read out of an NFC tag, etc. Other methods are also possible.

In some variations, it may be beneficial to use information from previous consumption events to determine or predict what a user is consuming during a new consumption event. A data storage unit may store a database with records of consumption events. Each record contains values of at least one or more features related to the consumption event and at least one or more labels related to the consumption event. A consumption event record may include other information as well. In this example, the feature set comprises a "meal signature," as it identifies/characterizes the meal.

A dataset of raw data from sensors, wearable devices and processors for the monitoring system might distill data down to a set of features that are directly or indirectly related to a consumption event, thus allowing sensor data to be compressed, simplified and possibly be more easily processed. Features may include day of week of the event, time of the event, duration of the event, location of the event, metrics related to pace, metrics related to quantities used or consumed, metrics related to methods, utensils or equipment used, etc. For example if the event is an eating event, features may include metrics related to the pace of eating, metrics related to quantities consumed, eating method(s) such as eating with spoon, fork or fingers, etc. Other features are also possible. Features from other non-hand gesture sensors such as heart rate sensors, motion sensors, temperature sensors, audio sensors, or blood pressure sensors are also possible. Features may also include location information (e.g., from a GPS system), calendar information, and inputs from applications the user uses or interacts with.

Food/drink type, brand or content information or meal descriptors might constitute the "labels" for the consumption event records in the database. The dataset in the database may be used to train a classifier to predict food content or meal descriptors (labels) from the features. Labels for the consumption event dataset used for training may be obtained from manual entry by a user, may be based on the analysis of an image of the food, may be based on information obtained from the read out of an NFC tag, etc. Other methods are also possible.

The processing and analysis subsystem may use statistics, machine learning or artificial intelligence techniques to determine or predict the food(s) being consumed in the present eating event. The processing and analysis subsystem may store all previously recorded foods in a database and for the present eating event assign a confidence level to each of the food(s) in the database using statistics, machine learning or artificial intelligence. Other analytics methods are also possible. Based on the confidence levels, the processing and analysis subsystem then makes a determination as to what the food is that is being consumed or that is most likely being consumed. A confidence level might be for a decision on whether or not an event occurs, but also might be a decision on which of multiple possibilities more likely occurred. For example, there might be that one of four events occurred and there is a confidence score associated with each of the four events and the event with the highest confidence score is presumed to be the event that occurred.

When a new consumption event occurs or some time after the occurrence of a new consumption event, the feature values may be derived from the event detection subsystem. Features may be entered in a detector that uses the trained classifier model. The detector assigns a confidence level to each food content label or meal descriptor in the database.

More than one food or drink may be consumed during a consumption event. Additional processing of the gestures within a single consumption event may be required to determine which gestures are related to what food or drink item. For example, if a person is drinking a can of soda while eating nuts, the consumption event may have 2 labels: "can of soda" and "nuts". Additional processing may be required to separate gestures related to drinking the can of soda from gestures related to eating nuts. The set of features for the consumption event may include features that relate specifically to the drinking soda event, features that relate specifically to the eating nuts event and/or features that relate to the combination of the eating and drinking event. Examples of the latter might be time of the consumption event, total duration of the overall consumption event, location information, etc. Other features are also possible. In the above example, the event detection system might determine that eating nuts and drinking a soda are all part of one event, that of having a meal or a snack.

The consumption event may be stored as a single entry in the database. The entry for the consumption event may include features that relate to the drinking soda event, features that relate to the eating nuts event and features that relate to the overall consumption event, including both the eating and drinking. The entry for the consumption event may include one or more labels that specifically relates to the eating nuts event, one or more labels that specifically relate to the drinking soda event and/or one or more labels that relate to the overall consumption event comprising eating and drinking.

In addition or instead of the entry for the overall consumption event, one or more entries may be created in the database that specifically relate to one of the events of "drinking soda" or "eating nuts." Such entries may include features that specifically relate to only one of the events and/or features that related to the overall consumption event (e.g., time, duration, location).

In another example, a consumption event may include eating soup with a spoon and eating pasta with a fork. In this case, all gestures are eating gestures, but the gesture recognition logic may distinguish and categorize gestures based on the eating method or utensil that was used, in this example: eating with a fork versus eating with a spoon.

The food logging system enables a high level of automation of the food journaling process. Once the food content associated with a consumption event that might comprise one or more events has been added to the database, it may be used in the future to determine or predict what a user is consuming or has consumed simply based on the "meal signature" (i.e., information related to the eating activity or behavior associated with the event) and without requiring the user to enter manually enter the food content again or without collecting that information through an object information retrieval subsystem.

For example, a system may record that a user ate a bagel, along with characteristics of that food intake event. Characteristics may include but are not limited to time of the event, the location of the user at time of the event, the number of bites, duration of the event, the eating method, the pace of eating, other events or behaviors occurring coinciding or otherwise related in time to the event etc. Other characteristics are also possible. The system may also record that at a different time, the user ate yoghurt, along with characteristics of that food intake event. The system may record a plurality of food intake events, its content and one or more of its characteristics and store as historical information in a database. The information may be stored in a data table. This data table can be used when later an event detection subsystem detects a food intake event and the characteristics of the food intake event can be compared to historical events information stored in the data table to determine with a certain confidence level the content and/or amount consumed by the user during the food intake event.

In some variations, records in the database may be subdivided into groups (e.g., based on meal type—breakfast, lunch, dinner, snack) and a different model may be used for each subgroup. Alternatively, the same model may be used but it may be trained using data from only one or a selective set of subgroups. In other variations, instead of a supervised machine learning approach (i.e., where features are specified manually), unsupervised learning may be used instead. With unsupervised learning, the classifier will autonomously generate features from the raw dataset provided.

Information about a consumption event, obtained from the event detection subsystem, can be combined with information about the foods the user is consuming, and additional processing/analysis may be performed on the combined dataset to obtain additional information or insights about the activity/behavior that cannot be obtained from looking at only one of the data sources alone.

For example, information about the type or content of foods the user is consuming may be obtained from an object information retrieval subsystem, but may not provide any information how much of the food item is consumed or how fast the specific food item is being consumed. The pace and quantity in turn may be derived from data received from event detection subsystem 101. By combining the information from both subsystems, it becomes possible to derive a more comprehensive and accurate model of a subject's actual activities and behaviors. For example, it may be useful to know that a user is drinking from a can of regular soda, but it may also be important to know how much the user drinks. For example, it possible that the user does not finish the can of soda. Knowing how much of the can of soda the user consumes may be important to more accurately calculate caloric intake or sugar intake.

In the above manner, key characteristics of a consumption event, as well as content being consumed, are recorded without or with minimal user intervention.

In specific embodiments, the systems and methods here might be used in connection with a planned meal program or therapy that the user may have chosen, been recommended or been prescribed. In that case, a meal signature can be used, possibly combined with other data, to monitor and/or confirm that a user is compliant with the planned meal program or therapy. A system or program executed on a device that is local to the user or on a remote server may analyze a user's meal signature, compare it to the meal signature of the corresponding planned meal and make a determination as to whether or not the user has complied with the planned meal protocol. The determination may use one or more features of the meal signature, such as for example, the date and time of the eating event, the pace of eating, the amount of food consumed, the content of the food consumed, they timing, amount and/or content of the fluid consumed with the meal, the location of meal consumption, features related to the heart rate of the user before, during and/or after the eating event. Other features are also possible.

Application: Inventory Tracking/Replenishment

The monitoring system may be used to determine how much of an object has been used/consumed, determine when a user may be running out of a certain object, or predict when a user will run out. This information may be fed into an automatic reordering or replenishment system.

The monitoring system may be used to monitor and track inventory of objects or items that can be linked to specific activities or behaviors. Such objects or items may include but are not limited to foods, drinks, toothpaste, tooth floss, hand soap, shampoo, lipstick, mascara, cigarettes, medications, shaving cream. Alternatively, the system may also be used to track inventory of living organisms such as animals or humans.

When an event detection system detects the occurrence of one or more specified activities or behaviors, it may notify an object information retrieval system. The object information retrieval system can then be used to obtain information about the objects or items that the subject is interacting with. This information may include the brand, model, content size, manufacturing date, purchase date, expiration date. Other information may also be collected.

In one embodiment of the present disclosure, the processing and analysis subsystem combines information from event detection subsystem 101 with information from object information retrieval subsystem 102 to track how much a subject is consuming of a specific object and determine that a subject is running out or has run out of said object supply, or predict when a subject is likely to run out of said object supply.

For example, event detection subsystem detects and tracks each time a user brushes his teeth. Upon detection of a tooth brushing event, the object information retrieval system gets activated and collects information about the toothpaste being used (brand, model, tube size, etc.). The event detection subsystem knows/tracks how often a tooth brushing occurs and possibly also how much toothpaste is consumed during each event (alternatively, the system may assume a pre-configured "standard serving size" for each tooth brushing event). Information from the event detection subsystem and the object information retrieval system, may be combined to determine how much toothpaste has been used, is left in the tube, determine when a user is about to run out or has run out or predict when a user is likely to run out. By monitoring how often a subject brushes his or her teeth and by collecting the brand and content size information of the toothpaste container, the processing and analysis subsystem can determine that a subject is running out of toothpaste or predict when a subject is likely to run out of toothpaste. This output of the processing and analysis subsystem can be linked to a reordering or replenishment system.

Extra steps could be that the monitoring system stores a database of objects that a user may be using or consuming. This database may be populated with items retrieved from a shopping list, with items scanned in by a user (e.g., using a bar code, QR code, etc.). Other examples to import items into a list are also possible. The content size of an object or the number of items in a package is also recorded. For example, the database may be comprised of records, where each record may include one or more of the following data elements: product brand, product model, content size.

Each time an event is detected, information about the object that is consumed or used as part of the event is retrieved. A processing or analysis engine that is part from the monitoring system verifies if the object(s) are in the database. If an object is found in the database, the processing and analysis system computes an estimate for the amount of the object that was used or consumed during the present event. The processing and analysis system may estimate the remaining content size by subtracting the estimated amount consumed from the amount recorded in the database. It may then update the amount in the database to match the new remaining content size taking into account the amount that was consumed or used during the most recent event.

When the amount in the database drops below a configured threshold, and alert or notification may be issued to activate a reordering or replenishment process. For example, a notification may be sent to a user. Alternatively, the monitoring system may send a signal to a central server that manages a user's online shopping account. The central server may be 3rd party-owned server and the communication between the monitoring system and the central server may be encrypted and may require one or more authentication steps. In response to a reordering input from the monitoring system, a processing unit associated with the central server may analyze the input and add the relevant object(s) to the user's shopping cart. The central server may notify the user that an item has been added to his/her cart. Alternatively, the order may automatically be processed.

In a variation, the processing and analysis system of a monitoring system may use historical data about the consumption of a specific object to predict when a user will run out of said object. For example, the processing and analysis system may look at the average rate of change of the content over time, or may apply higher order curve fitting to compute a function or equation that reflects the rate of change of the content of said object over time.

Similar examples may apply to smoking/cigarettes left in pack, drinking from cans/how many cans of soda consumed, eating bars/how many bars consumed, etc.

In another example, event detection subsystem may detect that a user is smoking. It may furthermore determine additional information such as puff count. When a smoking event is detected, the object information retrieval subsystem may be activated and provide information about the brand, cigarette count, nicotine levels or other relevant information about the pack of cigarettes. By monitoring how often or how much a subject is smoking and by collecting the brand and cigarette count information of the pack of cigarettes, the processing and analysis subsystem can determine that a subject is running out of cigarettes or predict when a subject is likely to run out of cigarettes. This output of the processing and analysis subsystem can be linked to a reordering or replenishment system. Other examples are also possible. The monitoring system may be linked to an automatic or semi-automatic reordering or replenishment system. The reordering or replenishment system may be at a remote location and may be implemented on a remote server that can be accessed via the Internet.

Application: Production Line Monitoring/QC Automation

The monitoring system described in the first section may be used for quality control purposes on a production line. Detection of a hand motion that is indicative of a production line operator performing a specific action or executing a specific procedure. Upon detection of such event, object information collection subsystem (e.g., using NFC) may collect information about objects/items that operator may be interacting with. This could be information about parts on an assembly line, the part number of the finished part, etc. This may be recorded in a central system that maps operator to finished part IDs, maps finished part to lot numbers of individual parts, etc. The central system may link this information to data retrieved from a Quality Control system. This may provide information about performance of a specific operator.

Application: Medication Adherence

Since the event system is able to monitor events and gestures and determine consumption, this can be used to automatically monitor a medication administration protocol that defines when medication needs to be taken and with what foods or other actions. This may be with specific meal categories such breakfast, at certain times of day, etc. A medication administration protocol might specify if patient should eat or drink with medication. Optionally, the medication administration protocol may also specify how much food or liquid patient should consume.

For example, when medication needs to be taken at certain times of day, a medication adherence system can monitor the time and when it is time to take medication issues an alert. It may then also activate the event detection subsystem (if it is not yet already active) and start monitoring the outputs of the event detection subsystem. It waits for a notification confirmation from user that he/she has taken the medication.

If a confirmation is received and if medication administration protocol prescribes that medication needs to be taken with food or liquid, the medication adherence system monitors the outputs from eating/drinking event detection subsystem and determines if rules specified by medication administration protocol are met. This could be as simple as confirming that an eating or drinking event has occurred with or shortly after the intake of the medication. In case the medication administration protocol specifies that a minimum amount of food or fluid needs to be consumed, the medication adherence system may monitor the additional outputs of the event detection subsystem (metrics related to quantities consumed) to confirm that this condition is met. Different rules/logic to determine if medication administration protocol has been met are also possible.

If no confirmation is received, the medication adherence subsystem may issue a second notification. Additional notifications are also possible. After a pre-configured number of notifications, the medication adherence subsystem may issue an alert. Alert me be issued to user as a text message, or may be sent to a remote server over the internet or over a cellular connection (e.g., to hospital, caregiver).

If medication needs to be taken with specific meal categories, the medication adherence system may monitor the outputs of an eating detection subsystem. When an eating event is detected, it will use logic to determine the applicable meal category. If the meal category matches the category described by the medication administration protocol, it will issue a notification to remind the user to take his/her medication. If the medication administration protocol prescribes that food or liquid should be consumed with the medication, the monitoring logic outlined above may be implemented to determine that the medication administration protocol has been adhered to.

The medication adherence system may monitor the outputs of an eating event detection subsystem to determine if the start of an eating event has occurred and determine if the eating event is of the applicable meal category. When an eating event is detected and the meal category matches the category described by the medication administration protocol, certain actions might be taken, such as that it may activate an object information retrieval system (e.g., NFC tags, imaging) to collect more information about the objects the user is interacting with. In this way, it may obtain information about the medication from an NFC tag attached to the pill box or medication container. In another use, it may verify that the medication matches the medication prescribed by the medication administration protocol and/or issue a notification to remind the user to take his/her medication. If the medication administration protocol prescribes that food or liquid should be consumed with the medication, the monitoring logic outlined above may be implemented to determine that the medication administration protocol has been adhered to.

The system might also incorporate details about the medication obtained from the object information collection system or through a different method in the notification, record confirmations in response to the notification from user that he/she has taken the medication, ask the user for additional information about the medication, and/or send the user a follow-on question at a pre-configured time after the user has taken the medication to get additional inputs. (e.g., query about how the user is feeling, query about pain levels, prompt to measure blood sugar level).

Application: Insulin Therapy/Meal-Aware Artificial Pancreas

The system might be used to detect onset of eating/drinking to start administering micro-doses of insulin. An insulin dosage calculator can take into account glucose level at start of eating, a slope of glucose level at start of eating to determine dosage and timing of insulin delivery. Insulin may be delivered at once or in multiple micro-doses.

If additional information about food is obtained from object information retrieval subsystem (e.g., drinking a can of regular soda versus diet soda), this information may be taken into account by the insulin dosage calculator. For example, if a food item with high sugar content is being consumed, the insulin dosage calculator may increase the dosage administered per micro-dosing event or may increase the number of micro-doses being delivered in a given period of time.

In a specific embodiment, the system might be used to detect onset of eating or drinking to retrieve data from a blood glucose meter or continuous glucose monitoring ("CGM") device equipped with a wireless technology. The system may collect one or more glucose readings. If no recent readings are available, it may prompt or remind a user to take a measurement. Alternatively, upon detection of the onset of eating or drinking, the system may prompt or remind a user to take a measurement. The system may subsequently retrieve the measurement data from the glucose meter using a wireless link.

An insulin management system may use the inputs from the event detection system and/or the glucose readings to make an insulin dosage decision or recommendation. The recommendation may be communicated to the user, for example in a notification or other message. The system may subsequently interact with a connected insulin delivery device such as an insulin pen or an insulin pump to confirm if the recommended dosage, a dosage different from the recommended dosage or no dosage has been administered. The system may send another message to the user to remind the user again or recommend a different dosage. The system may store the data from the event detection subsystem, the glucose meter and/or the insulin delivery devices.

Alternatively, the system may use the inputs from the event detection system and/or the glucose readings and interact with a connected insulin pen or connected insulin pump to initiate an insulin dosage administration without user intervention.

In yet another embodiment, an insulin management system may process one or more inputs from the event detection system and one or more readings from a glucose meter of CGM to determine if a patient is treating a hypoglycemic event.

Application: Control of External Devices or Objects within User's Surroundings

As explained herein, an event detection system can send a trigger signal to an ancillary system to perform a possibly or apparently unrelated act. As an example, when an actual, imminent or probable binge eating event is detected, the detection may be used to control a lighting system to change the tone/intensity of the light in the room to positively influence behaviors, start playing a particular genre of music, a particular song, music from an artist selected by the user at an earlier time or at or near the time of the event, change the temperature of a room, or other response that need not be specific to the event detection system, but that has some effect that, independent of the ancillary system, is desired. As a result, it is not required for the ancillary system to be aware of why various actions are being triggered and the ancillary system does not need to be specifically programmed or designed to work as part of an event response and feedback system.

These interactions with connected external objects can be seen as behavioral interventions, but can happen autonomously or semi-autonomously, to create more advanced experiential interventions that are personalized and contextualized.

Application: Dynamic Adjustment of Interventions

The detection of the start of an event (e.g., eating, drinking, smoking event) or of certain characteristics or behaviors associated with the event (e.g., pace of eating, pace of inhales when smoking) can trigger a message to be sent to the user. The message can, for example, be sent as a notification on the user's wearable device. The user may be notified that a message is being sent by means of an audio signal or by means of haptic feedback. Other mechanisms to inform the user that a message has been sent are also possible.

The message can have an educational or promotional content, be a prompt, a reminder, a coaching tip, etc. In some embodiments, the user can confirm that he or she has received and/or read the message, for example with a button press, by means of selection of a displayed action button on a touch display on the wearable device, by means of a voice input using a microphone, or with a specific hand movement that is understood by the system as a user confirmation.

In other embodiments, the system may infer that the user is reading or has read the message without explicit user confirmation. For example, if the message is displayed on a user's wristworn wearable device, a system may analyze the user's wrist movement and/or rotation following the sending and display of the message, e.g., by analyzing the data from one or more motion sensors in the wearable device, to determine if and/or for how long the user is looking at his/her display on the wearable following the sending of the message. From this analysis, the system can then determine or infer if the user is reading or likely reading, or has read or is likely to have read the message.

The message can also be a request for user input. As an example, when a start of an eating event is detected, the system may send a message to ask the user to rate his hunger level, assess the healthiness of his food choices, or assess her emotional state. The system may record whether or not the user responds, the actual user response, and the time it took for the user to respond.

Explicit user confirmation or user responses as well as inferred user actions (such as inferring that the user read or likely read the message) can be recorded and analyzed to measure the level of user engagement or changes in level of user engagement at a given time, or over a certain time window. The data can be analyzed to determine the level of user engagement to messages in general, and/or to assess the level of user engagement in response to one or more specific message types, specific message content, specific message intensity or specific message tone. The information and insights about a user's engagement with messages in general or with specific messages or message types can be recorded in a database that records data and information about a user, and can be used to adjust the content, tone, intensity, etc. of future messages and user interventions.

Survey Component

The event detection system might include a survey component. Since the event detection system knows when an event is going to occur or is occurring, the event detection system can time a survey question for the user. For example, the event detection system might ask the user just before an eating or smoking event starts or shortly after it starts to answer a survey question, such as "what were your emotions before you started this event?" or "what triggered you to start this event?" and thus provide just-in-time impressions of the user that the user, caregiver, or software program or healthcare maintenance or disease management system can later review or process to learn more about associations between events and states of mind. This is likely to be more accurate than, say, a weekly e-mail survey asking the user "when each of the events in the last week began, what were you feeling?". Since the event detection system is accurately predicting and detecting particular events, and recording their timestamps, it can easily present real-time, in-the-moment surveys.

User Engagement

A feedback system might assess the level of user engagement to evaluate what message types, content, intensity, or tone a user best responds to. This information can then be used by the feedback system to further customize the messages for the specific user.

In other variants, the assessment of level of user engagement at a given time or over a time window, optionally combined with additional information such as for example the user's responses to certain messages, or data retrieved from other applications such as a user's calendar, can used by a feedback system to assess a user's motivation and/or a user's readiness for acting on the information delivered in the message. A feedback system may use this to dynamically adjust the type, content, tone or intensity/frequency of its messages. For example, if a feedback system determines that a user is not motivated or ready to act (e.g., the user might be distracted by another event developing in his life), the feedback system may decide to scale back on the frequency of the messages it sends, to soften the tone of the messages, to change the content of one or more messages. On the other hand, when a feedback system determines that a user is highly engaged, as inferred from a high level of engagement with messages sent to the user, it may increase the frequency of the messages, increase the complexity level of one or more coaching tips, etc.

Figure 3:
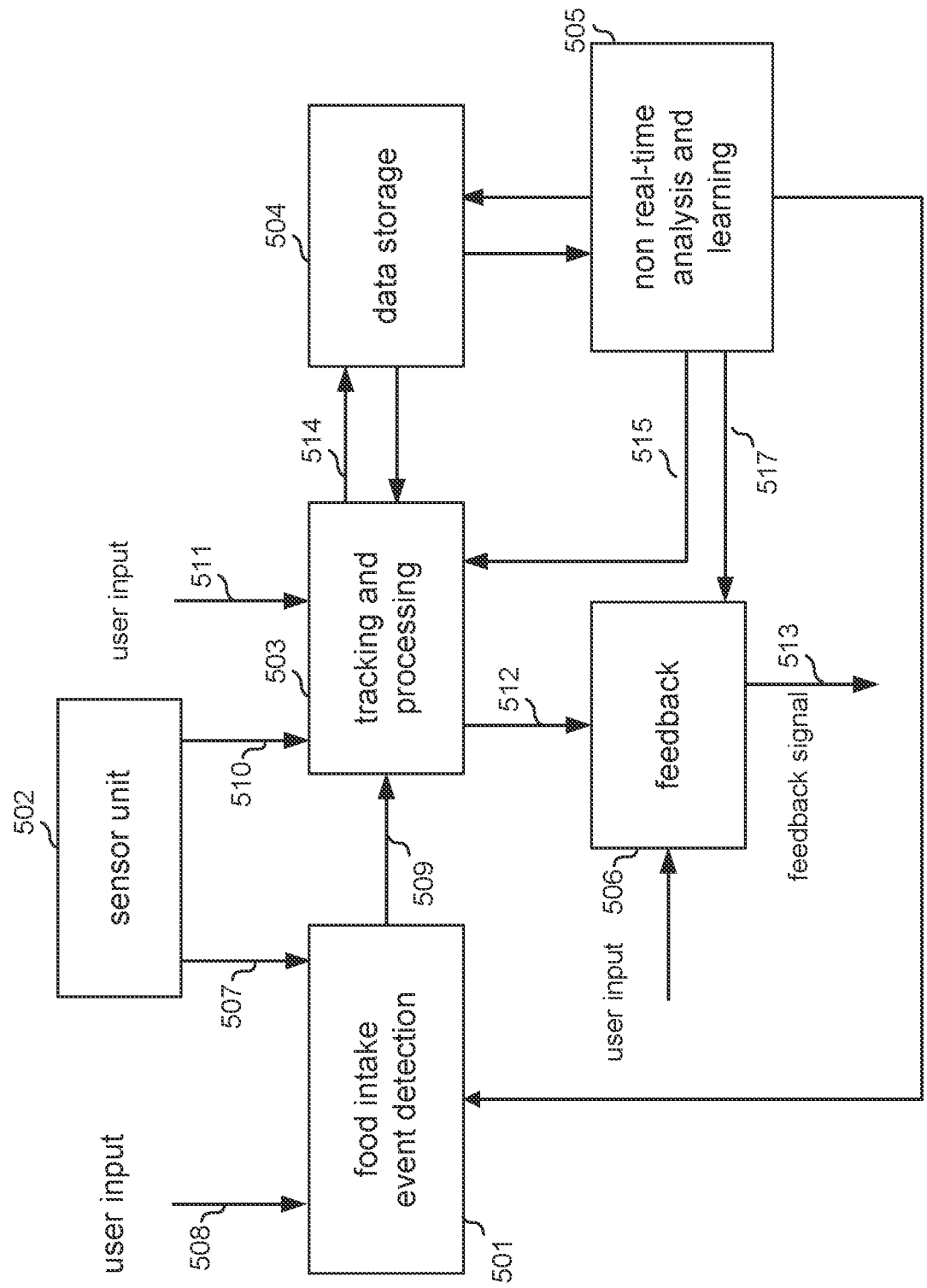
FIG. 3 is an illustrative example of an environment in accordance with at least one embodiment.

FIG. 3 shows a high level functional diagram of a dietary tracking and feedback system in accordance with an embodiment of the present invention. A system for dietary tracking and feedback may in part include one or more of the following: a food intake event detection subsystem 501, one or more sensors 502, a tracking and processing subsystem 503, a feedback subsystem 506, one or more data storage units 504 and a learning subsystem that might perform non-real-time analysis. In some embodiments, elements shown in FIG. 3 are implemented in electronic hardware, while in others some elements are implemented in software and executed by a processor. Some functions might share hardware and processor/memory resources and some functions might be distributed. Functionality might be fully implemented in a sensor device, or functionality might be implemented across the sensor device, a processing system that the sensor device communicates with, such as a smartphone, and/or a server system that handles some functionality remote from the sensor device. For example, a wearable sensor device might make measurements and communicate them to a mobile device, which then uploads them over the Internet to a server that further processes the data. Data or other information may be stored in a suitable format, distributed over multiple locations or centrally stored, in the form recorded, or after some level of processing. Data may be stored temporarily or permanently.

A first component of the system illustrated in FIG. 3 is the food intake event detection subsystem 501. The role of this subsystem is to identify the start and/or end of a food intake event and communicate an actual, probable or imminent occurrence of the start and/or end of a food intake event to other components in the system.

In general, the device detects what could be the start of a food intake event or the probable start of a food intake event, but the device would work sufficient for its purposes so long as the device reasonably determines such start/probable start. For clarity, that detection is referred to as a "deemed start" of a food intake event and when various processes, operations and elements are to perform some action or behavior in connection with the start of a food intake event, it would be acceptable for those various processes, operations and elements to take a deemed start as the start even if occasionally the deemed start is not in fact a start of a food intake event.

In one embodiment, the detection and/or signaling of the occurrence of the deemed start of a food intake event coincides with the deemed start of a food intake event. In another embodiment, it may occur sometime after the deemed start of the food intake event. In yet another embodiment, it may occur sometime before the deemed start of the food intake event. It is usually desirable that the signaling is close to the deemed start of the food intake event. In some embodiments of the current disclosure, it may be beneficial that the detection and/or signaling of the deemed start of a food intake event occurs ahead of the start of said food intake event. This may for example be useful if a message or signal is to be sent to the user, a healthcare provider or caregiver ahead of the start of the food intake event as a coaching mechanism to help steer a user's food intake decisions or eating habits.

In a preferred embodiment of the present disclosure, the detection of the start and/or ending of a food intake event by the food intake event detection subsystem 501 happens autonomously and does not require any special user intervention. To accomplish this, the food intake event detection subsystem may use inputs 507 from one or more sensors 502. Sensors may include, but are not limited to, accelerometers, gyroscopes, magnetometers, magnetic angular rate and gravity (MARG) sensors, heart rate sensors, blood pressure sensors, image sensors, cameras, optical sensors, proximity sensors, pressure sensors, odor sensors, gas sensors, glucose sensors, Global Positioning Systems (GPS), and microphones.

Methods for autonomous detection may include, but are not limited to, detection based on monitoring of movement or position of the body or of specific parts of the body, monitoring of arm movement, position or gestures, monitoring of hand movement, position or gestures, monitoring of heart rate, monitoring of blood pressure, monitoring of finger movement, position or gestures, monitoring of swallowing patterns, monitoring of mouth and lips movement, monitoring of saliva, monitoring of movement of cheeks or jaws, monitoring of biting or teeth grinding, monitoring of signals from the mouth, the throat and the digestive system. Methods for detection may include visual, audio or any other types of sensory monitoring of the person and/or his or her surroundings. The monitored signals may be generated by the dietary tracking and feedback system. Alternatively, they may be generated by a separate system but be accessible to the dietary tracking and feedback system through an interface. Machine learning and other data analytics techniques may be applied to detect the start or probable start of a food intake event from the input signals being monitored.

In one example, the food intake detection system 501 may monitor the outputs of accelerometer and/or gyroscope sensors to detect a possible bite gesture or a possible sip gesture. Such gestures might be determined by a gesture processor that uses machine learning to distill gestures from sensor readings. The gesture processor might be part of the processor of the worn device or in another part of the system.

Gesture detection machine learning techniques as described elsewhere herein may be used to detect a bite gesture or sip gesture, but other techniques are also possible. The food intake detection system 501 may further assign a confidence level to the detected bite gesture or sip gesture. The confidence level corresponds to the likelihood that the detected gesture is indeed a bite or sip gesture. The food intake detection system may determine that the start of a food intake event has occurred based on the detection of a gesture and its confidence level without any additional inputs. For example, the food intake event detection system 501 may decide that the start of a food intake event has occurred when the confidence level of the bite or sip gesture exceeds a pre-configured threshold.

Alternatively, when a possible bite or sip gesture has been detected, the food intake event detection system 501 may use additional inputs to determine that the start or probable start of a food intake event has occurred. In one example, the food intake event detection system 501 may monitor other gestures that are close in time to determine if the start of a food intake event has occurred. For example, upon detection of a possible bite gesture, the food intake event detection system 501 may wait for the detection of another bite gesture within a certain time window following the detection of the first gesture and/or with a certain confidence level before determining that the start of a food intake event had occurred.

Upon such detection, the food intake detection system 501 may place one or more circuits or components into a higher performance mode to further improve the accuracy of the gesture detection. In another example, the food intake event detection system 501 may take into consideration the time of the day, or the location of the user to determine if the start or probable start of a food intake event has taken place. The food intake event detection system may use machine learning or other data analytics techniques to improve the accuracy and reliability of its detection capabilities. For example, training data obtained from the user and/or from other users at an earlier time may be used to train a classifier. Training data may be obtained by asking for user confirmation when a possible bite or sip gesture has been detected. A labeled data record can then be created and stored in memory readable by the gesture processor that includes the features related to the gesture, along with other contextual features, such as time of day or location. A classifier can then be trained on a labeled dataset comprised of multiple labeled data records set of labeled data records, and the trained classifier model can then be used in a food intake event detection system to more accurately detect the start of a food intake event.

In another embodiment, the food intake detection subsystem may use triggers to autonomously predict the probable start of a food intake event. Methods for autonomous detection of a probable start of a food intake event based on triggers may include, but are not limited to, monitoring of a person's sleep patterns, monitoring of a person's stress level, monitoring of a person's activity level, monitoring of a person's location, monitoring of the people surrounding a person, monitoring of a person's vital signs, monitoring of a person's hydration level, monitoring of a person's fatigue level, monitoring of a person's heart rate. In some cases, the food intake detection subsystem may monitor one or more specific trigger signals or trigger events over a longer period of time and, in combination with the non-real-time analysis and learning subsystem 505 apply machine learning or other data analytics techniques to predict the probable occurrence of a start of a food intake event.

For example, without any additional information, it can be very difficult to predict when a user will eat breakfast. However, if the system has a record over a number of days of one or more of the following: the user's wake up time and the day of the week, of a user's eating times and the day of the week, of a user's physical activity, heart rate, body temperature and/or blood pressure preceding eating times and the day of the week, the system can use that historical pattern in determining a likely time for the user to eat breakfast. Those records might be determined by the system, possibly with feedback from the user about their accuracy or those records might be determined by the user and input via a user interface of the system. The user interface might be the worn device itself or, for example, a smartphone app. As a result, the system can process correlations in the historical data to predict the time or time window that the user is most likely to have breakfast based on one or more of the following: the current day of week, the current time, at what time the user woke up, the user's current or recent heart rate, the user's current or recent blood pressure, the user's current or recent physical activity, the user's current or recent body temperature. Other trigger signals or trigger events may also be used by the non-real-time analysis and learning subsystem 505 to predict the time that a user will eat breakfast.

In another example, the non-real-time analysis and learning system 505 may, over a certain period of time record the stress level of a user. The stress level may, for example, be determined by monitoring and analyzing the user's heart rate or certain parameters related to the user's heart rate. The stress level may also be determined by analyzing a user's voice. The stress level may also be determined by analyzing the content of a user's messages or electronic communication. Other methods for determining the stress level are also possible. The non-real-time analysis and learning system 505 may furthermore, over the same period of time, record the occurrence of food intake events and certain characteristics of the food intake event such as the pace of eating, the quantity of food consumed, the time spacing between food intake events, etc. It may then be possible by analyzing the historical data of stress levels, the occurrence of food intake events and food intake event characteristics and by looking at correlations in the historical data of stress levels, the occurrence of food intake events and food intake event characteristics, to predict based on the current stress level the probability that a user will start a food intake event in a certain time window in the future, or predict what time window in the future, the user will be most likely to start a food intake event. It may also be possible to predict characteristics of said food intake event, such as for example pace of eating or quantity of consumption.

Predictive Behavior Signaling System

Figure 4:
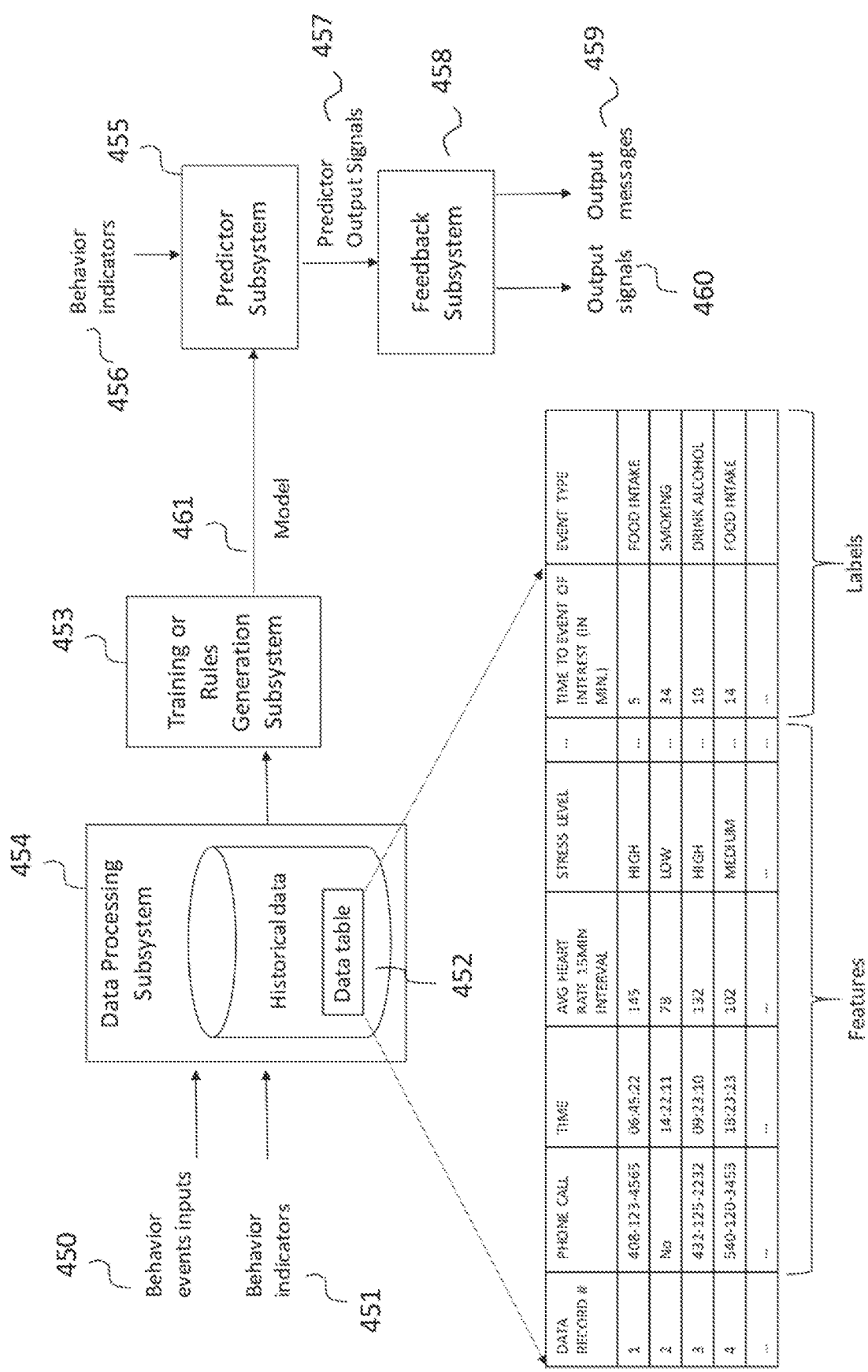
FIG. 4 illustrates a behavior event detection or prediction system that uses user historical data to determine when to send a signal or a message that relates to detected or predicted behavior events.

FIG. 4 illustrates an example of a behavior event prediction system that trains a predictor subsystem from past behavior events and past behavior indicator inputs to form a model and uses that model to predict or estimate a future behavior event from current behavior indicators. The behavior indicators have associated timestamps, as do the past behavior events, and the behavior event prediction system can provide an estimated time for occurrence of a future behavior event. Behavior indicators of a user can be derived from sensor inputs of sensors worn by the user, environmental sensors of the user's environment, interactions of the user with technological devices, and information processed, or likely processed by the user. By tracking the relative times of the past behavior indicators and the past behavior events, future behavior events could be predicted from current behavior indicators.

As shown there, data inputs from external sources, data inputs 451, are received by a data processing subsystem 454 and are tagged with their time of measurement or recording by the external data source. For example, if the data input are sensor readings from an external sensor, then those sensor readings are tagged with the time of the actual measurement by the sensor, a time close to the actual measurement of the sensor or a time related to the actual measurement of the sensor. The raw data from one or more sensor units may be sent directly to the predictive behavior signaling system. Alternatively, a processing unit external to the predictive behavior signaling system may first process the data before sending it to predictive behavior signaling system.

As shown in FIG. 4, a data processing subsystem 454 takes in behavior event inputs 450 and behavior indicator inputs 451 and stores it as a historical data set 452 that might be organized to include a data table as shown in FIG. 4 with the behavior indicator inputs tagged with a time relative to a corresponding behavior event and possibly a corresponding behavior type, if the system is handling multiple event types.

Note that the data table retains relative time data for indicators and events. For example, in the first data record, the behavior indicators are known to have occurred around five minutes prior to a behavior event. This data can be used to train a classifier model or otherwise define rules that the predictor subsystem will use to make a prediction (and possibly assign a confidence level to the prediction). This data would be passed from data processing subsystem 454 to training or rules generation subsystem 453 that might output a model or model parameter values 461 for a predictor subsystem 455.

Predictor subsystem 455 might take as input current behavior indicator inputs from which features for the data records in the data table were derived and apply the model or rules to those inputs to create an output prediction, possibly with an assigned confidence level, of a predicted future behavior event. Other characteristics of the prediction may also be included, e.g. if the prediction is that the user will start to eat in 20 minutes, the prediction output may also include how much the user is likely to eat or for how long he is likely to eat.

The output of a behavior event detection or prediction system may feed into a feedback system. The feedback system may have a set of rules and messages. Based on the output of the predictor subsystem, it may select one or more messages to feedback to a user or signal to another system.

An illustrative example of a predictive behavioral signaling system is shown in FIG. 4, as might be used to predict behavior as part of detecting events in advance, where those events relate to user behaviors. The system records occurrences of a behavior event of interest upon receiving behavior event inputs 450, and those inputs include timing information of the behavior event of interest. The system may also record additional characteristics of the behavior events. For example, if the behavior event of interest is food intake, the system may record timing information of food take event occurrences (e.g., start time, duration, end time). The system may also record additional characteristics of the occurrence (e.g., characteristics informative or indicative of pace of eating or drinking, number of bites or sips or other characteristics informative or indicative of amounts consumed, characteristics informative or indicative of content of meal or drink). In another example, the behavior of interest is smoking and the system may record timing information of smoking events (e.g., start time, duration, end time). The system may also record additional characteristics of the occurrence (e.g., characteristics informative or indicative of pace of smoking, number of inhales or other characteristics informative or indicative of amounts inhaled, characteristics informative or indicative of nicotine content). Other examples of behavior events are described elsewhere herein. Other examples are also possible.

The system can record data inputs 451 from external data sources and occurrences of behavior events of interest over a certain period of time. The duration of recording can vary, but it should be sufficiently long to create a training set. For example, it may record it over the duration of a week, a month, a year. It is also possible that it monitors and records on an on-going basis.

The data processing subsystem 454 may process one or more inputs from one or more external data sources and one or more records of behavior event occurrences to create a labeled data record of a training data set stored in data table 452. The data processing subsystem 454 aligns in time the inputs from external data sources and the occurrences of the behavior event of interest. The data processing subsystem 454 defines a time or a time window over which it will process data inputs from external sources. In one embodiment, the time or time window is referenced relative to the occurrence of a behavior event of interest. For example, the data processing subsystem may process data inputs from external data sources in a fixed time window leading up to the start of a behavior event occurrence (e.g., a 15-minute window 1 hour before the start of a behavior event occurrence). A plurality of time windows is also possible. (e.g., a 5-minute window, a 10-minute window, a 15-minute window and a 30-minute window with those time windows all having a starting, centered or ending time 1 hour before the start of a behavior event occurrence). Other examples are also possible. In another embodiment, the data processing subsystem may define one or more specific time or time window relative to the end of a behavior event occurrence. Other time references of the behavior event of interest are also possible. In another embodiment, the time or time windows are not specified relative to the occurrence of a behavior event of interest. Instead, they may be specified against an absolute time reference.

The data processing subsystem 454 processes data inputs from external data sources at the specified times or within the specified time windows to compute one or a plurality of characteristics or "feature values" for the labeled data record. For example, the external data source may be a set of timestamped heart rate sensor readings and the data processing subsystem 454 may use as features the minimum, maximum, average and/or changes in heart rate at the specified time or in the specified time windows relative to the behavior event occurrence. In another example, the external dataset may be a log of calendar entries and the data processing subsystem 454 may filter calendar entries that fall within one or more specified time windows relative to the occurrence of a behavior event of interest. The data processing subsystem 454 may do additional processing of those entries. For example, the data processing subsystem 454 may filter entries, or select specific information from those entries.

The data processing subsystem 454 may use the processed data as feature values in the labeled data record of the training data set.

The data processing subsystem 454 further assigns one or more labels to the labeled data record. Labels may have been assigned manually by a human or may have been generated automatically or semi-automatically. In a specific embodiment where a time or time window relative to the occurrence of a behavior event is used, a label can for example be the value of the time reference used to generate the features. For example, if the features are generated in a 15-minute time window 1 hour relative to the start of the behavior event of interest, a label value of "60 minutes" or "1 hour" may be assigned to the label of that data record. In a different embodiment, for example when the time or time windows for feature generation are defined on an absolute time reference, a label may be a binary value indicative of whether or not the start of the behavior event of interest occurred at a specific time or within a specific time window following the time or time window over which the features were generated. Additional characteristics of the behavior event occurrence may also be used as labels. For example, if the behavior event is a food intake event, the pace of eating or the amount consumed may be added as labels. In yet another example, other characteristics such as whether or not the food intake event was a binge eating event may be added as a label. Other characteristics are also possible.

A labeled data record can be created and stored in memory readable by a processor.

The data processing subsystem 454 creates a plurality of labeled data records. For example, it may use a sliding time window(s) to generate a set of labeled data records. A classifier can then be trained on a labeled dataset comprised of multiple labeled data records, and the trained classifier model can then be used in a predictive behavior signaling system to predict the start of a behavior event of interest. Multiple labeled data records may be stored in a data table.

The system further includes a predictor subsystem 455. The predictor subsystem 455 processes later data inputs 456 from external data sources to generate the feature values for data inputs 456. The predictor subsystem 455 analyzes the characteristics or "feature values" of new data inputs 456 to generate a prediction output. For example, the predictor subsystem 455 may feed the feature values into a trained classifier model to generate a prediction output. In another example, predictor subsystem 455 may apply a rules analyzer with rules derived by a rules generation subsystem 453. Other examples are also possible. In one specific embodiment, the output signal 457 might be a prediction of time until the start of the next occurrence of a behavior event of interest. In another embodiment, the prediction output signal 457 may be a binary output whether or not a behavior event of interest will happen at or within a specified time. In yet another embodiment, the prediction output signal 457 may be a confidence level or probability that a behavior event of interest will happen at or within a given time. In yet another embodiment of the disclosure, the prediction output is prediction of time until the start of the next occurrence of a behavior event of interest along with a confidence level of the prediction. In yet another embodiment, the prediction output is prediction of time until the start of the next occurrence of a behavior event of interest along with additional characteristics of the predicted event. If the behavior event is a food intake event, the additional characteristics may for example be the predicted duration of food intake, the predicted amount of food consumption, etc. Other examples are also possible. The predictor subsystem 455 may process data inputs from external sources in real-time or near real-time. Alternatively, there may be a delay between the time the data inputs are generated, fed into the system and/or processed by the prediction subsystem.

A behavior event of interest can be a food intake event, a smoking event, a dental hygiene event, a medication intake event, a personal hygiene event, a physical activity event, a stress indicating event such as for example nail biting, making a phone call, driving a car. Other examples are also possible.

In one specific embodiment, the system predicts the occurrence of a behavior event. In other embodiments, the system may predict the occurrence of a behavior event with specific characteristics. The system may for example be used to predict a binge eating episode or stress snacking. In another example, the system may be used to predict under-hydration or malnutrition.

The above description assumes a training subsystem that uses data records with features and labels to train a classifier model. Alternatively, a neural network may be used to autonomously derive characteristics and parameters of the data inputs without explicit feature generation. It is also possible that a different system is used to generate one or more rules to be used by the predictor subsystem to determine one or more predictor output signals.

Output signals 457 may be used by feedback subsystem 458 to trigger a message to a user or a signal to an ancillary system. For example, when a predictor subsystem predicts that a user will likely incur a binge eating episode in the next 15 minutes, the output 457 may be used by feedback subsystem 458 to send a message or instruction 459 to a room environmental control system to instruct the room environmental control system to cool the room by three degrees. In the more general case, feedback subsystem 458 outputs output messages 459 to users and/or outputs output signals 460 to ancillary devices, each in response to a trigger based on a behavior event or a predicted behavior event. In another example, when a predictor subsystem predicts that a user will likely light up a cigarette and start smoking in the next half hour, this may be signaled to a feedback subsystem 458 through predictor output signal 457, and feedback subsystem 458 may send a message to the user, for example to invite the user to reach out to a caregiver to get help.

In a specific embodiment of the disclosure, a non-real time analysis and learning system is part of a predictive meal signaling system. The non-real time analysis and learning system may record data from one or more data sources along with the occurrence of and characteristics of a user's food intake events over a period of time. The data sources may for example be heart rate, hydration level, stress level. But other data sources are also possible. The period of time over which data is collected may vary as well. It could for example be over several days, several weeks, several months. The collection of data may also be on-going, and not be limited to a specific period of time. In that case, the new data may be fed into the system periodically or from time to time to improve, or otherwise modify or adjust certain parameters or the accuracy of the system. As an example, the non-real time analysis and learning system may record a user's data such as heart rate, stress level, hydration level, body temperature, transpiration level, etc. over time. It may process and analyze that data or one or more subsets of that data over one or more specific time windows referenced in time to the start of a food intake event, relative to the end of a food intake event, and/or relative to other timing characteristics of the food intake event. For example, a non-real time analysis and learning system may analyze the heart rate data in a time window preceding the start of a food intake event.

In an example described below, there is a set of sensors, or at least inputs from a set of sensors, coupled to a machine classification system that outputs gesture data from sensor readings, taking into account rules and stored data derived from training the machine classification system. A training subsystem might be used to train the machine classification system and thereby forming the stored data derived from training. Each of these components might use distinct hardware, or shared hardware, and can be localized and/or remote. In general, when a gesture is detected, a system can analyze that gesture, determine likely actual, probable or imminent activities or behaviors and provide the user feedback with respect to those activities or behaviors. For example, a vibration as a feedback signal to indicate that the user has previously set up the system to alert the user when the user has been drinking for a semi-continuous period of more than 45 minutes or that the user has reached their target for the amount of walking to be done in one session.

Various rule sets could be employed that map behavior events to signals/messages output by a system that predicts or detects behavior events so that the system might output control signals to ancillary devices that will perform actions that prevent certain behaviors that were predicted, or that are desired responses to certain behaviors, or that send messages to the user or others to prepare for possible predicted behavior.

The behavior prediction system might determine when to send a signal or a message that relates to detected or predicted behavior events. In some embodiments, historical data is used, whereas in other embodiments, the historical data is analyzed in advance and distilled down to rules that can be stored in a messages and rules database. As one example, if the event detection or prediction system were to detect or predict the start of a smoking event and there was historical data that included references to receipt of a telephone call from a particular number at some time before a smoking event, that might be distilled down to "Send the user a message two minutes after ending a call with person P1 saying 'You wanted to be notified of triggers in your efforts to reduce smoking. You typically start smoking four minutes after receiving a call from P1. That was two minutes ago.' and record the user's response."

In either case, whether the processing is done in advance or at the time of sending a signal/message, the data table might contain parameters that correspond behavior indicators from sensed activity or environmental details, a timestamp of when those parameters occurred and an indication (a timestamp or a time relative to the timestamp of the sensed activity or details) of when the event being triggered or initiated might occur. Since the data table includes not only the item but an indication of the timing of the item relative to the event that they precede, this can be used to develop, with varying levels of confidence, the prediction that a particular event is about to start. For example, if a heart rate sensor detects a rapid increase in heart rate for a short duration without significant body motion of the user and also detects an eating event starting 20 minutes thereafter and the data table 406 contains several data items corresponding to behavior indicators, such as "short heart rate burst; 20 minutes prior", "short heart rate burst; 21 minutes prior", and "short heart rate burst; 20 minutes prior", from previous eating events that followed heart rate bursts, when a future heart rate burst occurs, the event detection system might flag that behavior indicator as an advance signal of an eating event that may start 20 minutes in the future from that behavior indicator's timestamp. The actual value presented for the predicted start of the eating event need not be exact, but could be useful even if the actual eating event occurred at a slightly different time.

The prediction could be used to trigger a message to the user or a signal to an ancillary system. For example, where the heart rate burst is known to be related to stress, the event detection system might send out a signal to a room environmental control system 10 minutes after the behavior indicator (an estimated 10 minutes before an expected eating event start) to instruct the room environmental control system to cool the room by three degrees.

In this manner, the data table could grow to a large dataset and might be combined with datasets of other users to identify patterns for use in predicting possible events. The behavior indicators might relate to gestures detected (user's hand unscrewing a bottle top, picking up a utensil, etc.), biometric readings (breathing, heart rate, skin temperature), location, computer interactions (read an e-mail from a particular person, was on a particular social media website, etc.), lighting, time of day. Each of the behavior indicators has a timestamp and, following analysis and processing, an estimated time for a future event, such as an eating event. From several such behavior indicators, the event detection system might be able to determine when the event will likely start and possibly a confidence value as to how certain the event is to occur around that time. As explained elsewhere herein, that information can result in a message or signal to an ancillary device to respond to the event.

In some embodiments of the present disclosure, the machine classification system may include additional subsystems or modified versions of the subsystems shown in FIG. 4. For example, if the behavior of interest is food intake, then the data input may include data records of a user's food intake events, with characteristics of each event. Characteristics may be a timestamp corresponding to the start of the food intake event, information related to the duration of the food intake event, average pace of eating, etc. Other characteristics are also possible.

The behavior indicators may include one or more time-stamped data inputs from external data sources that might relate to eating events or other types of events that are events to be detected. Such data might be computerized information, such calendar details like meetings and activities extracted from one or more calendars of the user, such as the time, duration, location, subject or agenda, classification (personal, business, etc.), participant details, telephone details (user's phone calls such as the time, duration, phone number(s), name(s) or other information of caller or call participant(s)). Other info might be information derived from or inferred from phone calls or other recorded conversations such as insights derived or inferred from the tone, intensity, choice of words, emotions, volume, etc. Yet other information might include location information, e.g., information obtained from a GPS system, inputs from one or more sensor units, including but not limited to body temperature sensor, heart rate sensors, blood glucose sensors, sensors measuring transpiration, information about a user's physical activity, mental health or stress level, or sleep, information about a user's activity or behaviors, including but not limited to food intake, smoking, dental hygiene activities such as flossing or brushing teeth, personal hygiene, driving a vehicle, making a phone call. Other data sources are also possible.

Data Structures for Data Analysis Used for Predicting Events

The notifications and interactions with the user can be customized according to the timing of events as the event detection system is able to, with limited inputs, determine the start of an event, or the future time of an event starting, with some confidence level, and take action accordingly. For example, if the event detection system determines with a certain confidence level that at a time 15 minutes in the future, the user might begin a binge eating event, the event detection system might output a message or a signal to an ancillary system in order to alter the occurrence of the predicted event(s). In another example, if the event detection system determines with a certain confidence level that an eating event has begun, it can signal an ancillary system such as an insulin microdosing apparatus to begin releasing insulin. This would be an improvement over a messaging system that uses fixed times for presenting user messages or that only sends signals much later than the start of an event.

In the more general case, for behavior events, there is an anchor time, which might be the start time, the end time, a peak time or another time relative to the event, from which responses to the event are timed. For example, a response for a behavior event might be emitted zero minutes or three minutes after the anchor time of the behavior event and the anchor time might be the start of the event or two minutes after the start of the event. Instead of minutes being the unit of measure of the response time or the anchor time, other units might be used, such as number of bites, number of sips, number of inhales, etc.

Additional Details

In specific embodiments, the non-real time analysis and learning subsystem may use historical data from different users, or a combination of data from other users and from the wearer, and use similarities between one or more of the different users and the wearer, such as age, gender, medical conditions, etc., to predict the probable start of a food intake event by the wearer.

In yet other examples, the non-real-time analysis and learning subsystem 505 may use methods similar to the methods described herein to predict when a user is most likely to relapse in a binge eating episode or is most likely to start stress snacking or convenience snacking.

Sensors and Machine Learning

A variety of sensors may be used for such monitoring. The monitored signals may be generated by the dietary tracking and feedback system. Alternatively, they may be generated by a separate system but be accessible to the dietary tracking and feedback system for processing and/or use as trigger signals. Machine learning and other data analytics techniques may also be applied to predict some other characteristics of the probable intake event, such as the type and/or amount of food that will likely be consumed, the pace at which a person will likely be eating, the level of satisfaction a person will have from consuming the food, etc.

The machine learning process performed as part of gesture recognition might use external data to further refine its decisions. This might be done by non-real-time analysis and learning subsystem process. The data analytics process might, for example, consider the food intake events detected by the gesture-sensing based food intake detection system and the gesture-sensing based tracking and processing system, thus forming a second layer of machine learning. For example, over a period of time, food intake events and characteristics related to those food intake events are recorded, such as eating pace, quantity of food consumption, food content, etc., while also tracking other parameters that are not directly, or perhaps not obviously, linked to the food intake event. This could be, for example, location information, time of day a person wakes up, stress level, heart rate, blood pressure, certain patterns in a person's sleeping behavior, calendar event details including time, event location and participant lists, phone call information including time, duration, phone number, etc., email meta-data such as time, duration, sender, etc. The data analytics process then identifies patterns and correlations. For example, it may determine a correlation between the number of calendar events during the day and the characteristics of the food intake event(s) in the evening. This might be due to the user being more likely to start snacking when arriving home, or that dinner is larger and/or more rushed when the number of calendar event(s) for that day exceeds a certain threshold. With subsystem 505, it becomes possible to predict food intake events and characteristics from other signals and events that are not obviously linked to food intake. Additional contextual metadata such as location, calendar information, day of week or time of day may be used by the processing and analysis subsystem to make such a determination or prediction.

Processing and analysis of one or more sensor inputs, and/or one or more images over longer periods of time, optionally using machine learning or other data analytics techniques may also be used to estimate the duration of a food intake event or may be used to predict that the end of a food intake event is probable or imminent.

In another embodiment, some user input 508 may be necessary or desirable to properly or more accurately detect the start and/or end of a food intake event. Such user input may be provided in addition to external inputs and inputs received from sensors 502. Alternatively, one or more user inputs may be used instead of any sensor inputs. User inputs may include, but are not limited to activating a device, pressing a button, touching or moving a device or a specific portion of a device, taking a picture, issuing a voice command, making a selection on a screen or entering information using hardware and/or software that may include but is not limited to a keyboard, a touchscreen or voice-recognition technology. If one or more user inputs are required, it is important that the user interaction is conceived and implemented in a way that minimizes the negative impact on a person's normal activities or social interactions.

A food intake event detection subsystem may combine multiple methods to autonomously detect predict the actual, probably or imminent start and/or end of a food intake event.

Another component of the system is the tracking and processing subsystem 503. In a preferred embodiment of the present disclosure, this subsystem interfaces 509 with the food intake event detection subsystem 501, and gets activated when it receives a signal from the food intake event detection subsystem that the actual, probable or imminent start of an event has been detected, and gets disabled when or sometime after it receives a signal from the food intake event detection subsystem that the actual, probable or imminent ending of an event has been detected. Upon detection of the start of a food intake event, the device might trigger activation of other sensors or components of the food intake tracking system, and might also trigger the deactivation of those upon detection of the end of the food intake event.

In another embodiment of the current disclosure, the tracking and processing subsystem may be activated and/or deactivated independent of any signals from the food intake detection subsystem. It is also possible that certain parameters be tracked and/or processed independently of any signals from the food intake detection subsystem, whereas the tracking and/or processing of other parameters may only be initiated upon receiving a signal from the food intake event detection subsystem.

Figure 5:
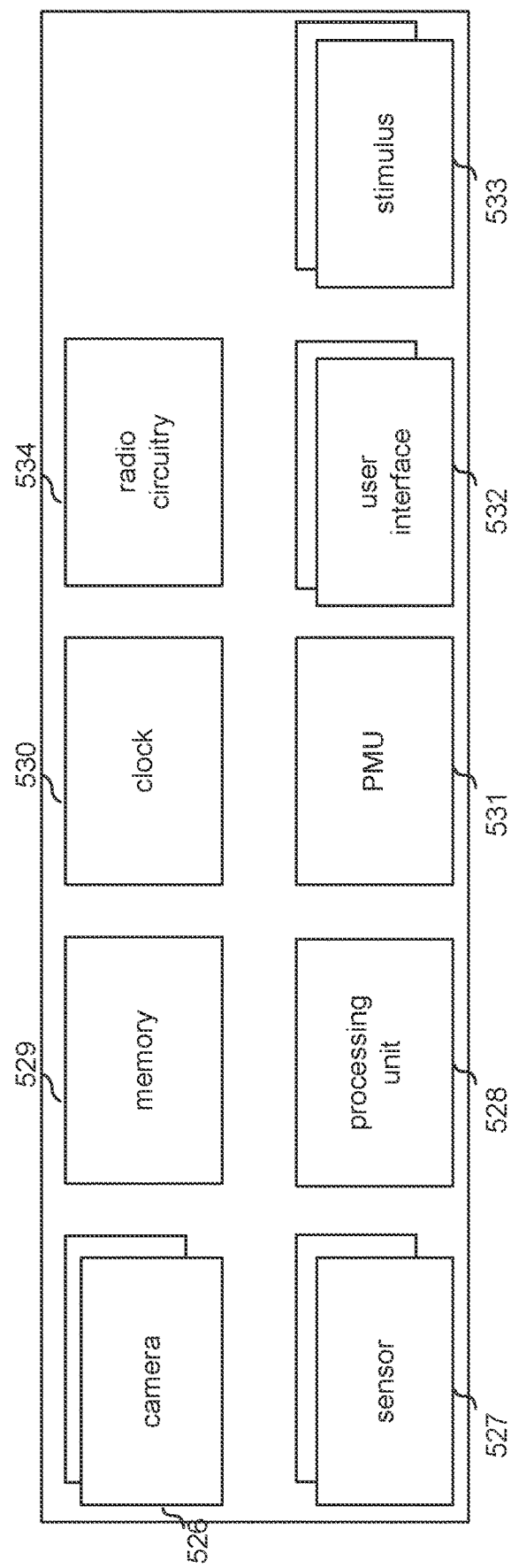
FIG. 5 illustrates some of the components disposed in an electronic device, in accordance with one embodiment.

FIG. 5 illustrates some of the components disposed in an electronic device, in accordance with one embodiment. The electronic device typically includes, in part, one or more sensor units 527, a processing unit 528, memory 529, a clock or crystal 530, radio circuitry 534, and a power management unit ("PMU") 531. The electronic device may also include one or more camera modules 526, one or more stimulus units 533 and one or more user interfaces 532. Although not shown, other components like capacitors, resistors, inductors may also be included in said the electronic device. Power Management unit 531 may, among other things, include one or more of the following: battery, charging circuitry, regulators, hardware to disable the power to one or more components, power plug.

In many embodiments, the electronic device is a size constrained, power-sensitive battery operated device with a simple and limited user interface. Where power is limited, the electronic device might be programmed to save power outside of behavior events. For example, a processor in the electronic device might be programmed to determine the start of a behavior event, such as an eating event, and then power up additional sensors, place certain sensors in a higher performance mode and/or perform additional computations until the processor determines an end of the behavior event, at which point the processor might turn off the additional sensors, place certain sensors back in a lower performance mode and omit the additional computations.

For example, the processor might be programmed to disable all motion-detection related circuitry, with exception of an accelerometer. The processor could then monitor accelerometer sensor data and if those data indicate an actual or prominent food intake activity such as a bite or sip gesture, then the processor could activate additional circuitry, such as a data recording mechanism. The processor might use the accelerometer sensor data to monitor a pitch of the wearer's arm.

For example, the processor might measure pitch of the wearer's arm until the pitch exceeds a certain threshold, perhaps one indicative of a hand or arm movement towards the wearers' mouth. Once that is detected, the processor can change the state (such as by changing a memory location set aside for this state from "inactive" or "out-of-event" to "in an action" or "in-event") and activate additional circuitry or activate a higher performance mode of specific circuitry or components. In another embodiment, other accelerometer sensor data characteristics such as first integral of acceleration (velocity) or the second integral of acceleration (distance traveled), or characteristics related to or derived from the first and/or second integral of acceleration might be used, as determined from one or more accelerometer axis. A machine learning process might be used to detect specific movements and translate those to gestures.

An end of a food intake event might be detected by the processor by considering whether a certain time has expired since a last bite or sip movement or when other data (meta-data about the wearer, motion-detection sensor data, and/or historical data of the wearer, or a combination of those). Based on those, the processor makes a determination that a food intake event is not likely and then changes the state of the electronic device to an inactive monitoring state, possibly a lower power mode.

The lower power mode might be implemented by the processor reducing the sampling rate of the accelerometer and/or gyroscope, powering down the gyroscope, reducing the update rate at which sensor data is transferred from the electronic device to a support device, compressing the data before transferring the data from the sensing electronic device to the support device.

In some embodiments of the present disclosure, some of the components that are shown in FIG. 5 as separate components may be combined. As an example, the processing unit, memory, radio circuitry and PMU functionality may entirely or in part be combined in a single wireless microcontroller unit ("MCU"). Other combinations are also possible. Similarly, components that are shown as a single component in FIG. 5 may be implemented as multiple components. As an example, the processing functionality may be distributed across multiple processors. Likewise, data storage functionality may be distributed across multiple memory components. Other examples of distributed implementations are also possible.

In another embodiment of the present disclosure, the radio circuitry may not be present and instead a different interface (such as for example a USB interface and cable) may be used to transfer data or information to and/or from the electronic device.

Stimulus unit 533 may provide feedback to the user of the electronic device. A stimulus unit 533 may include but is not limited to a haptic interface that applies forces, vibrations or motions to the user, a speaker or headphones interface that provides sounds to the user, and a display that provides visual feedback to the user.

In certain embodiments, the processing and analysis of signals from sensors embedded in the electronic device can detect when electronic device has been disabled, tampered with, removed from the body or is not being used. This can be used to conserve power, or to send a notification to the user, a friend or another person who might directly or indirectly have an interest in being notified if the electronic device is not being used properly.

Description Detection/Prediction of Start/End of Food Intake Event

In a preferred embodiment, the electronic device is worn around the wrist, arm or finger and has one or more sensors that generate data necessary to detect the start and/or end of a food intake event. The electronic device may also be integrated in a patch that can be attached to a person's arm or wrist. The electronic device may also be a module or add-on device that can be attached to another device that is worn around the wrist, arm or finger. Sensors used to detect the start and/or end of a food intake event may among other sensors include one or more of the sensors described herein.

The raw sensor outputs may be stored locally in memory 529 and processed locally on processing unit 528 to detect if the start or end of a food intake event has occurred. Alternatively, one or more sensor outputs may be sent to the electronic device and/or a central processing and storage unit, either in raw or processed format, for further processing and to detect if the start or end of a food intake event has occurred. Regardless of where the processing for food intake detection occurs, sensor outputs in raw or processed format may be stored inside the electronic device, inside the electronic device and/or inside the central processing and storage unit.

The sensor or sensors that generate data necessary for the detection of the start and/or end of a food intake event may be internal to the electronic device. Alternatively, one or more of the sensors responsible for the detection of the start of a food intake event may be external to the electronic device, but are able to relay relevant information to the electronic device either directly through direct wireless or wired, communication with the electronic device or indirectly, through another device. It is also possible that the electronic device and the external sensor or sensors area able to relay information to the electronic device, but are not able to relay information to one another directly.

In case of indirect communication through another device such as a mobile phone or other portable or stationary device, such third device is able to receive data or information from one or external sensor units, optionally processes such data or information, and forwards either the raw or processed data or information to the electronic device. The communication to and from the electronic device may be wired or wireless, or a combination of both.

Examples of sensors that may be external to the electronic device may be one or more sensors embedded in a necklace or pendant worn around the neck, one or more sensors embedded in patches that are attached to a different location on the body, one or more sensors embedded in a supplemental second wearable device that is worn around the other arm or wrist or on a finger of the other hand, or one or more sensors integrated in a tooth. In some embodiments, the electronic device is worn on one hand or arm but detects movement of the other hand or arm. In some embodiments, electronic devices are worn on each hand.

Information obtained from a non-real-time analysis and learning subsystem may also be used, optionally in combination with information from one or more sensors 527, to predict or facilitate the detection of a probable, imminent or actual start/end of a food intake event.

It is often desirable that the detection and/or the prediction of the start and/or end of a food intake event happens autonomously without requiring user intervention. For example, if the actual, probable or imminent start of a food intake event is predicted or detected autonomously, this information can be used as a trigger to activate or power up specific components or circuits that are only needed during a food intake event. This can help conserve power and extend the battery life of the electronic device. The prediction or detection of an actual, probable or imminent start of a food intake event can also be used to issue a cue or reminder to the user. A cue can for example be sent to the user to remind him/her to take further actions including, but not limited to, logging the food intake event or taking a picture of the food. Upon detection of the start of a food intake event, one or more cues, possibly spread out over the duration of the food intake event, to remind the user that a food intake event is taking place and improving in-the-moment awareness and/or encourage mindful eating. Cues or reminders may for example be sent through discrete haptic feedback using one or more stimulus units 533. Other methods using one or more user interfaces 532, such as for example one or more LEDs, a display message, or an audio signal, are also possible. Alternatively, a mobile device may be used to communicate cues, reminders or other information such as for example portion size recommendations or alternative suggestions to eating to the user.

If the actual, probable or imminent end of a food intake event is predicted or detected autonomously, this information can be used as a trigger to power down or at least put in a lower power mode one or more circuits or components of the electronic device that are only needed during a food intake event. This can help conserve power and extend the battery life of the electronic device. The detection of the actual, probable or imminent end of a food intake event may also be used to modify or suspend the feedback provided to the user by one or more stimulus units 533, by one or more of the user interfaces 532, and/or by a mobile device.

In some embodiments of the present disclosure, the detection or prediction of the actual, probable or imminent start and/or end of a food intake event may not be entirely autonomously. For example, the user may be required to make a specific arm, wrist, hand or finger gesture to signal to the electronic device the actual, probable or imminent start and/or end of a food intake event. The arm, wrist, hand or finger gesture is then detected by one or more sensors inside the electronic device. It is usually desirable that the arm, wrist, hand or finger gesture or gestures required to indicate the start and/or end of a food intake event can be performed in a subtle and discrete way. Other methods may also be used. For example, the user may be asked to push a button on the electronic device to indicate the start and/or end of a food intake event. Voice activation commands using a built-in microphone. Other methods are also possible.

Description of Tracking of Eating Behaviors and Patterns

In a particular embodiment, the electronic device is worn around the wrist, arm or finger and has one or more sensors that generate data that facilitate the measurement and analysis of eating behaviors, patterns and habits. Sensors used for measuring and analyzing certain eating behaviors and patterns may include one or more of the sensors described herein.

Relevant metrics that may be used to quantify and track eating behaviors and eating patterns may include, but are not limited to, the time between subsequent bites or sips, the distance between the plate and the user's mouth, the speed of arm movement towards and/or away from the user's mouth, and the number of bites or sips during a single food intake event, derived from the total count of arm movements corresponding to a bite or sip, specific chewing behavior and characteristics, the time between taking a bite and swallowing, amount of chewing prior to swallowing.

In some embodiments, the generation, collection and/or processing of data that facilitate the measurement and analysis of eating behaviors, patterns and habits may be continuously, periodically or otherwise independently of the start and/or end of a food intake event. Alternatively, the generation, collection and/or processing of data that facilitate the measurement and analysis of eating behavior and patterns may occur only during a food intake event or be otherwise linked to a specific food intake event. It is also possible that some sensor data are being generated, collected and/or processed continuously, periodically or otherwise independently of the start and/or end of a food intake event whereas other sensor data are taken during a food intake event or otherwise linked to a food intake event.

In some embodiments, one camera may be used to capture one or more images of food items that are on a plate, table or other stationary surface, and a second camera may be used to capture one or more images of food items that are being held by the user, such as for example finger foods or drinks. The use of more than one camera may be desirable in situations where no user intervention is desirable and the position, area of view or focal range of a single camera is not suite to capture all possible meal scenarios.

In one example embodiment, the position, the orientation and the angle of view of the camera are such that an image or video capture is possible without any user intervention. In such an embodiment, the wearable device may use a variety of techniques to determine the proper timing of the image or video stream capture such that it can capture the food or a portion of the food being consumed. It may also choose to capture multiple images or video streams for this purpose. Techniques to determine the proper timing may include, but are not limited to, the following: sensing of proximity, sensing of acceleration or motion (or absence thereof), location information. Such sensor information may be used by itself or in combination with pattern recognition or data analytics techniques (or a combination of both) to predict the best timing for the image or video capture. Techniques may include, but are not limited to, training of a model based on machine learning.

DETAILED DESCRIPTION OF SPECIFIC EMBODIMENTS

In one specific embodiment of the present disclosure, the electronic device is a wearable device in the form factor of a bracelet or wristband that is worn around the wrist or arm of a user's dominant hand. The electronic device is a mobile phone and central processing and storage unit is one or more compute servers and data storage that are located at a remote location.

Figure 6:
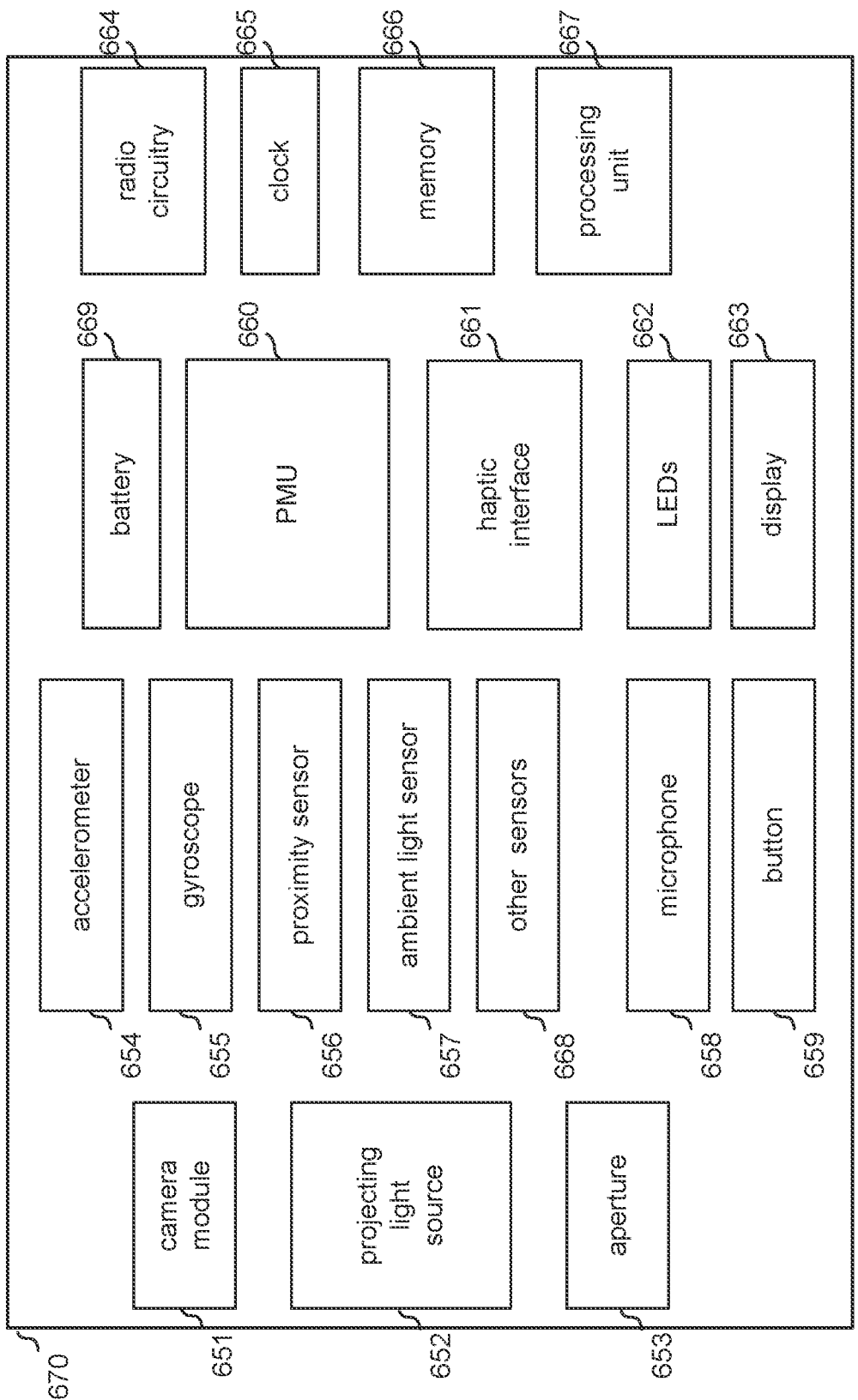
FIG. 6 illustrates elements of a wearable bracelet or wristband.

One possible implementation of a wearable bracelet or wristband in accordance with aspects of the present invention is shown in FIG. 6. Wearable device 670 may optionally be implemented using a modular design, wherein individual modules include one or more subsets of the components and overall functionality. The user may choose to add specific modules based on his personal preferences and requirements.

The wearable device 670 may include a processor, a program code memory and program code (software) stored therein and/or inside the electronic device to optionally allow users to customize a subset of the functionality of wearable device 670.

Wearable device 670 relies on battery 669 and Power Management Unit ("PMU") 660 to deliver power at the proper supply voltage levels to all electronic circuits and components. Power Management Unit 660 may also include battery-recharging circuitry. Power Management Unit 660 may also include hardware such as switches that allows power to specific electronics circuits and components to be cut off when not in use.

When there is no behavior event in progress, most circuitry and components in wearable device 670 are switched off to conserve power. Only circuitry and components that are required to detect or help predict the start of a behavior event may remain enabled. For example, if no motion is being detected, all sensor circuits but the accelerometer may be switched off and the accelerometer may be put in a low-power wake-on-motion mode or in another lower power mode that consumes less power than its high performance active mode. The processing unit may also be placed into a low-power mode to conserve power. When motion or a certain motion pattern is detected, the accelerometer and/or processing unit may switch into a higher power mode and additional sensors such as for example the gyroscope and/or proximity sensor may also be enabled. When a potential start of an event is detected, memory variables for storing event-specific parameters, such as gesture types, gesture duration, etc. can be initialized.

In another example, upon detection of motion, the accelerometer switches into a higher power mode, but other sensors remain switched off until the data from the accelerometer indicates that the start of a behavior event has likely occurred. At that point in time, additional sensors such as the gyroscope and the proximity sensor may be enabled.

In another example, when there is no behavior event in progress, both the accelerometer and gyroscope are enabled but at least one of either the accelerometer or gyroscope is placed in a lower power mode compared to their regular power mode. For example, the sampling rate may be reduced to conserve power. Similarly, the circuitry required to transfer data from the electronic device to the electronic device may be placed in a lower power mode. For example, radio circuitry 664 could be disabled completely. Similarly, the circuitry required to transfer he data from the electronic device to another electronic device may be placed in a lower power mode. For example, it could be disabled completely until a possible or likely start of a behavior event has been determined. Alternatively, it may remain enabled but in a low power state to maintain the connection between electronic devices but without transferring sensor data.

In yet another example, all motion-detection related circuitry, including the accelerometer may be switched off, if based on certain meta-data it is determined that the occurrence of a particular behavior event such as a food intake event is unlikely. This may for example be desirable to further conserve power. Meta-data used to make this determination may, among other things, include one or more of the following: time of the day, location, ambient light levels, proximity sensing, and detection that wearable device 670 has been removed from the wrist or hand, detection that wearable device 670 is being charged. Meta-data may be generated and collected inside wearable device 670. Alternatively, meta-data may be collected inside the mobile phone or inside another device that is external to wearable device 670 and to the mobile phone and that can either directly or indirectly exchange information with the mobile phone and/or wearable device 670. It is also possible that some of the meta-data are generated and collected inside wearable device 670 whereas other meta-data are generated and collected in a device that is external to wearable device 670. In case some or all of the meta-data are generated and collected external to wearable device 670, wearable device 670 may periodically or from time to time power up its radio circuitry 664 to retrieve meta-data related information from the mobile phone or other external device.

In yet another embodiment of the invention, some or all of the sensors may be turned on or placed in a higher power mode if certain meta-data indicates that the occurrence of a particular behavior event, like for example a food intake event is likely. Meta-data used to make this determination may, among other things, include one or more of the following: time of the day, location, ambient light levels and proximity sensing. Some or all of the meta-data may be collected inside the mobile phone or inside another device that is external to wearable device 670 and to the mobile phone and that can either directly or indirectly exchange information with the mobile phone and/or wearable device 670. In case some or all of the meta-data are generated and collected external to wearable device 670, wearable device 670 may periodically or from time to time power up its radio circuitry 664 to retrieve meta-data related information from the mobile phone or other external device.

The detection of the start of a behavior event, such as for example a food intake event may be signaled to the user via one of the available user interfaces on wearable device 670 or on the mobile phone to which wearable device 670 is connected. As one example, haptic interface 661 inside wearable device 670 may be used for this purpose. Other signaling methods are also possible.

The detection of the start of a behavior event such as for example a food intake event may trigger some or all of the sensors to be placed or remain in a high-power mode or active mode to track certain aspects of a user's eating behavior for a portion or for the entirety of the food intake event. One or more sensors may be powered down or placed in a lower power mode when or sometime after the actual or probable end of the behavior event (the deemed end of the behavior event) has been detected. Alternatively, it is also possible that one or more sensors are powered down or placed in a lower power mode after a fixed or programmable period of time.

Sensor data used to track certain aspects of a user's behavior, such as for example a user's eating behavior, may be stored locally inside memory 666 of wearable device 670 and processed locally using processing unit 667 inside wearable device 670. Sensor data may also be transferred to the mobile phone or remote compute server, using radio circuitry 664, for further processing and analysis. It is also possible that some of the processing and analysis is done locally inside wearable device 670 and other processing and analysis is done on the mobile phone or on a remote compute server.

The detection of the start of a behavior event, such as for example the start of a food intake event, may trigger the power up and/or activation of additional sensors and circuitry such as for example the camera module 651. Power up and/or activation of additional sensors and circuitry may happen at the same time as the detection of the start of a food intake event or sometime later. Specific sensors and circuitry may be turned on only at specific times during a food intake event when needed and may be switched off otherwise to conserve power.

It is also possible that the camera module only gets powered up or activated upon explicit user intervention such as for example pushing and holding a button 659. Releasing the button may turn off the camera module again to conserve power.

When the camera module 651 is powered up, projecting light source 652 may also be enabled to provide visual feedback to the user about the area that is within view of the camera. Alternatively, projecting light source 652 may only be activated sometime after the camera module has been activated. In certain cases, additional conditions may need to be met before projecting light source 652 gets activated. Such conditions may, among other things, include the determination that projecting light source 652 is likely aiming in the direction of the object of interest, or the determination that wearable device 652 is not moving excessively.

In one specific implementation, partially depressing button 659 on wearable device 670 may power up the camera module 651 and projecting light source 652. Further depressing button 659 may trigger camera module 651 to take one or more still images or one or more streaming images. In certain cases, further depressing button 659 may trigger a de-activation, a modified brightness, a modified color, or a modified pattern of projected light source 652 either before or coinciding with the image capture. Release of button 659 may trigger a de-activation and/or power down of projected light source 652 and/or of camera module 651.

Images may be tagged with additional information or meta-data such as for example camera focal information, proximity information from proximity sensor 656, ambient light levels information from ambient light sensor 657, timing information etc. Such additional information or meta-data may be used during the processing and analysis of food intake data.

Various light patterns are possible and may be formed in various ways. For example, it may include a mirror or mechanism to reflect projecting light source 652 such that projected light source 652 produces one or more lines of light, outlines the center or boundaries a specific area, such as a cross, L-shape, circle, rectangle, multiple dots or lines framing the field of view or otherwise giving to the user visual feedback about the field of view.

One or more Light Emitting Diodes (LEDs) may be used as project light source 652. The pattern of visible light may, among other things, be used by the user to adjust the position of the camera, adjust the position the object of interest and/or remove any objects that are obstructing the line of sight between the object of interest and the camera.

Projected light source 652 may also be used to communicate other information to the user. As an example, the electronic device me use inputs from one or more proximity sensors, process those inputs to determine if the camera is within the proper distance range from the object of interest, and use one or more light sources to communicate to the user that the camera is within the proper distance range, that the user needs to increase the distance between camera and the object of interest, or that the user needs to reduce the distance between the camera and the object of interest.

The light source may also be used in combination with an ambient light sensor to communicate to the user if the ambient light is insufficient or too strong for an adequate quality image capture.

The light source may also be used to communicate information including, but not limited to, a low battery situation or a functional defect.

The light source may also be used to communicate dietary coaching information. As an example, the light source might, among other things, indicate if not enough or too much time has expired since the previous food intake event, or may communicate to the user how he/she is doing against specific dietary goals.

Signaling mechanisms to convey specific messages using one or more projecting light sources may include, but are not limited to, one or more of the following: specific light intensities or light intensity patterns, specific light colors or light color patterns, specific spatial or temporal light patterns. Multiple mechanisms may also be combined to signal one specific message.

Microphone 658 may be used by the user to add specific or custom labels or messages to a food intake event and/or image. Audio snippets may be processed by a voice recognition engine.

In certain embodiments, the accelerometer possibly combined with other sensors may, in addition to tracking at least one parameter that is directly related to food intake and/or eating behavior, also be used to track one or more parameters that are not directly related to food intake. Such parameters may, among other things, include activity, sleep or stress.

Examples of Using Context to Improve Overall Accuracy

Figure 7:
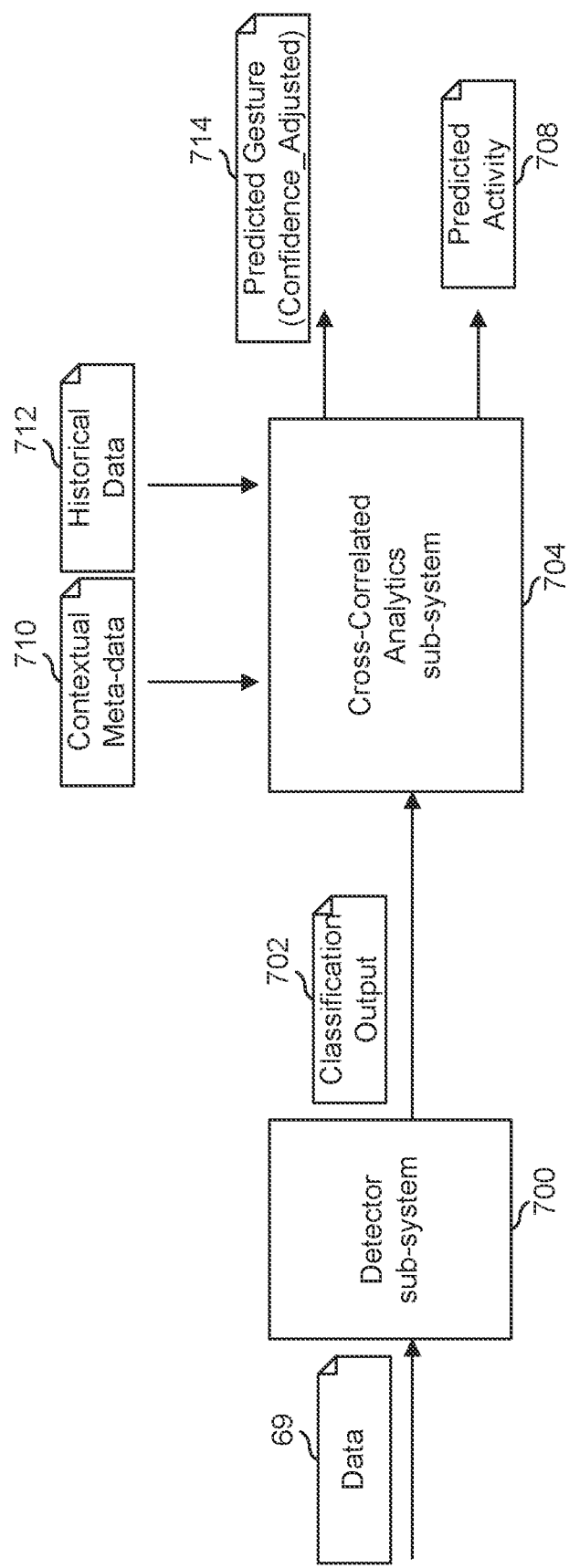
FIG. 7 shows an example of a machine classification system that includes a cross-correlated analytics sub-system.

FIG. 7 shows an example of a machine classification system that includes a cross-correlated analytics sub-system 704. Classification output 702 may be fed into cross-correlated analytics sub-system 704. Cross-correlated analytics sub-system 704 can make adjustments based one or more contextual clues to improve the accuracy. In the example of gesture recognition, an example of a contextual clue could be the proximity in time to other predicted gestures. For example, eating gestures tend to be grouped together in time as part of an eating activity such as a meal or a snack. As one example, cross-correlated analytics sub-system 704 could increase the confidence level that a predicted gesture is an eating gesture based on the confidence level and degree of proximity of nearby predictions.

In another embodiment, cross-correlated analytics sub-system 704 may take individual predicted gestures 714 from classification output 702 as inputs and may cluster individual predicted gestures into predicted activities 708. For example, cross-correlated analytics sub-system 704 may map multiple bite gestures to an eating activity such as a snack or a meal. Likewise, cross-correlated analytics sub-system 704 could map multiple sip gestures to a drinking activity. Other examples of activity prediction based on gesture clustering are also possible. Cross-correlated analytics sub-system 704 may modify the confidence level of a predicted gesture based on the temporal spacing and sequence of predicted activities. As an example, cross-correlated analytics sub-system 704 could decrease the confidence level that a predicted gesture is an eating gesture if it is detected shortly following or amid a "brushing teeth" activity. In another example, cross-correlated analytics sub-system 704 could decrease the confidence level that a predicted gesture is a drinking gesture if it is detected during or shortly after a brushing teeth activity. In this case, cross-correlated analytics sub-system 704 could decide to increase the confidence level that the gesture is a rinsing gesture.

Cross-correlated analytics sub-system 704 can adjust a classification output of a predicted gesture based on historical information 712 or other non-gesture meta-data 710 information such as location, date and time, other biometric inputs, calendar or phone call activity information. For example, cross-correlated analytics sub-system 704 may increase the confidence level that a predicted gesture is an eating gesture or a predicted activity is an eating activity if GPS coordinates indicate that the person is at a restaurant. In another example, cross-correlated analytics sub-system 704 may increase the confidence level that a predicted gesture is an eating gesture or a predicted activity is an eating activity if it occurs at a time of day for which past behavior indicates that the user typically engages in eating at this time of the day. In yet another example of the present disclosure, cross-correlated analytics sub-system 704 may increase the confidence level that a predicted gesture is an eating gesture or that a predicted activity is an eating activity if the predicted gesture or predicted activity is preceding or following a calendar event or phone call conversation if past behavior indicates that the user typically eats preceding or following similar calendar events (e.g., with same attendee(s), at certain location, with certain meeting agenda, etc.) or phone call conversation (e.g., from specific phone number). While the above examples reference eating, it will be apparent to one skilled in the art that this could also be applied to gestures other than eating. In the general case, the machine classifier with cross-correlated analytics sub-system uses contextual clues, historical information and insights from proximity sensing in time to improve accuracy, where the specific contextual clues, historical information and insights from proximity sensing in time and how they are applied is determined by methods disclosed or suggested herein.

In some embodiments of the present disclosure, Classification Output 702 may include additional features or gesture time envelope information. Cross-correlated analytics sub-system 704 may process such additional features or gesture time envelope information to determine or extract additional characteristics of the gesture or activity. As an example, in one embodiment of the present disclosure, cross-correlated analytics sub-system 704 derives the estimated duration of the drinking gesture from the gesture time envelope and this information can be used by cross-correlated analytics sub-system 704 or by one or more systems that are external to the machine classifier system to estimate the fluid intake associated with the drinking gesture.

In another embodiment, cross-correlated analytics sub-system 704 may derive the estimated duration of an eating gesture from the gesture time envelope and this information may be used by the cross-correlated analytics sub-system 704 or by one or more systems that are external to the machine classifier system to estimate the size of the bite associated with the eating gesture. Cross-correlated analytics sub-system 704 may combine the predicted drinking gestures with other sensor data to predict more accurately if someone is consuming a drink that contains alcohol and estimate the amount of alcohol consumed. Examples of other sensor data may include but are not limited to measuring hand vibration, heart rate, voice analysis, skin temperature, measuring blood, breath chemistry or body chemistry.

Detector sub-system 700 may predict a specific eating or drinking method and cross-correlated analytics sub-system 704 may combine the information obtained from detector sub-system 700 about specifics of the eating or drinking method with additional meta-data to estimate the content, the healthiness or the caloric intake of the food. Examples of eating/drinking methods may include but are not limited to eating with fork, eating with knife, eating with spoon, eating with fingers, drinking from glass, drinking from cup, drinking from straw, etc.). Examples of meta-data may include but are not limited to time of day, location, environmental or social factors.

Medication Dispensing System

Figure 8:
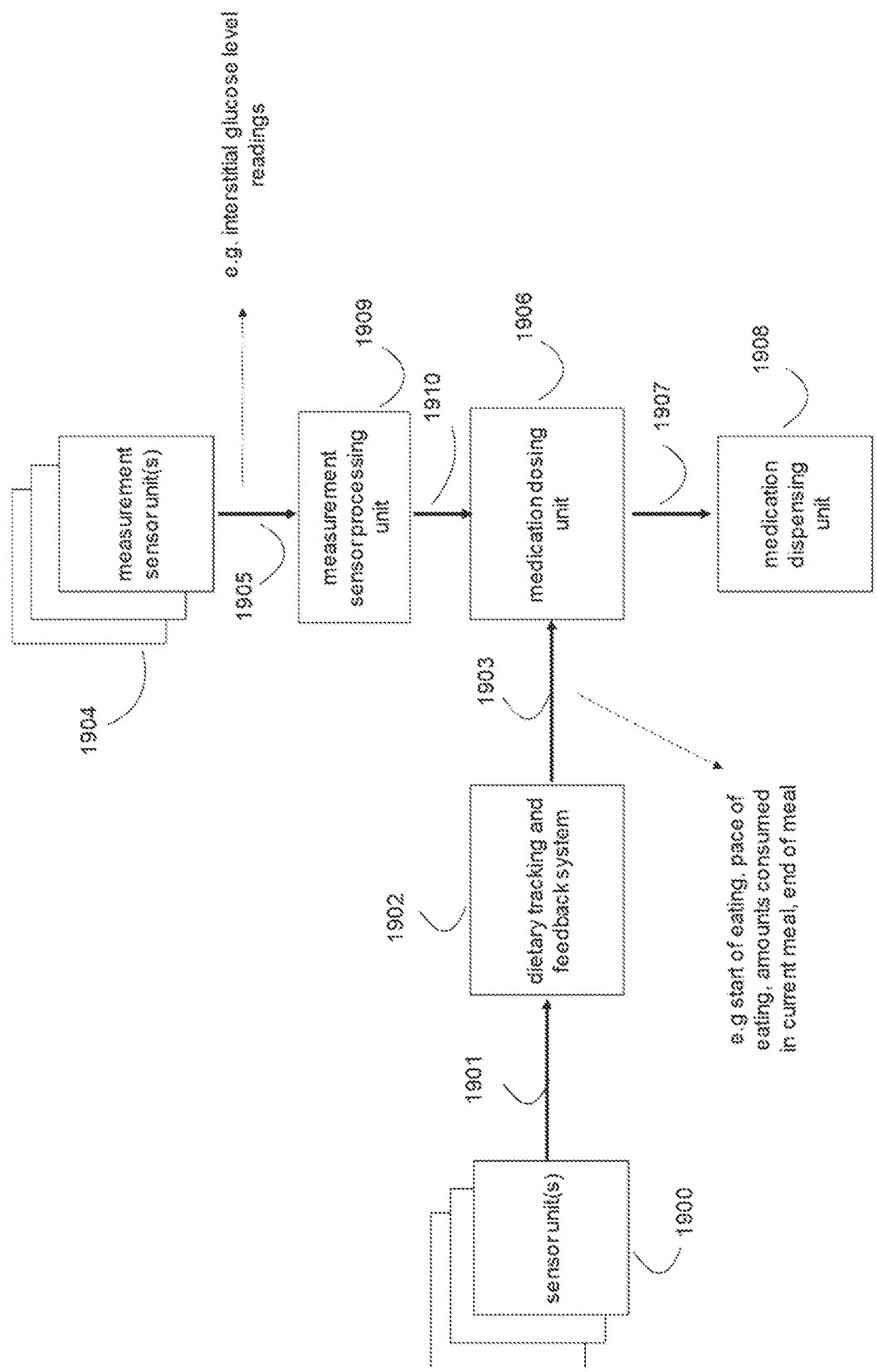
FIG. 8 shows a high level functional diagram of a medication dispensing system.

FIG. 8 shows a high level functional diagram of a medication dispensing system covered by the current disclosure. A medication dispensing system may in part include one or more of the following: a dietary tracking and feedback system 1902, one or more sensor units 1900, a measurement sensor processing unit 1909, a medication dosing unit 1906, one or more measurement sensor units 1904 and a medication dispensing unit 1908.

In one embodiment of the current disclosure, the medication to be administered is insulin, the measurement sensor unit 1904 is a continuous glucose monitor sensor that measures interstitual glucose levels, medication dispensing unit 1908 is an insulin pump and medication dosing unit 1906 is the insulin dosage computation unit of an automated insulin delivery system (a.k.a., artificial pancreas).

Each of the elements shown in FIG. 8 might be implemented by suitable structure. For example, these could be individual hardware elements or implemented as software structures in a wearable device, an ancillary device that communicates with a wearable device, or a server coupled over a network to the ancillary device and/or a wearable device. Some elements might be entirely software and coupled to other elements that are able to send and/or receive messages to or from the processor executing the software. For example, medication dispensing unit 1908 might be an embedded hardware system that injects microdoses of medication in response to instructions given by a software system and thus would only require minimal processing on-board.

Dietary tracking and feedback system 1902 maybe implemented as described elsewhere herein and may monitor the outputs of one or more sensor unit(s) to determine the actual, probable or imminent start of a food intake event. Upon detection of an actual, probably or imminent start of a food intake event, or some time thereafter, it may send a signal 1903 to medication dosing unit 1906 to inform medication dosing unit 1906 that an actual, probable or imminent start of a food intake event has been detected. Medication dosing unit 1906 may use this information to change its state to a "meal-in-progress" state.

Upon entering the meal-in-progress state or some time thereafter, medication dosing unit 1906 may calculate an initial meal medication dosage to be administered and send one or more messages to medication dispensing unit 1908. Alternatively, the medication dosage to be administered in connection with the start of a food intake event may have been pre-configured or calculated ahead of the occurrence of the food intake event. Upon receiving those messages 1907, medication dispensing unit 1908 may initiate delivery of the medication.

The medication dispensing unit may deliver the medication all at ones or according to a delivery schedule. The delivery schedule may be determined and communicated to the insulin delivery system by the medication dosing unit. The delivery schedule may be determined upon entering the meal-in-progress state or some time thereafter. The delivery schedule may also be pre-configured ahead of the occurrence of the food intake event.

The initial meal medication dosage and/or delivery schedule may cover the entire anticipated medication dosage for the food intake event. Alternatively, the initial meal medication dosage and/or delivery schedule may only cover a portion of the entire anticipated medication dosage for the food intake event, and additional medication dosages are expected at a later time during or after the food intake event.

Medication dosing unit 1906 may take into account additional inputs when calculating an initial medication dosage and or initial delivery schedule. Some inputs may be related to current or recent measurements, current or recent user activities and behaviors or other information corresponding to a current or recent state or condition of a user. Other inputs may be related to historical measurements, historical user activities and behaviors or other information corresponding to a past state or condition of a user.

Examples of Additional Inputs

Medication dosing unit 1906 may take into account one or more outputs 1910 from measurement sensor processing unit 1909. Medication dosing unit 1906 may perform additional processing steps on outputs 1910. For example, measurement sensor unit 1904 may be a continuous glucose monitor ("CGM"), and outputs 1910 of measurement sensor processing unit 1909 may be interstitual glucose level readings. Outputs 1910 may for example be updated every couple of minutes. Other update frequencies are also possible. Outputs 1910 may also be updated continuously. Medication dosing unit 1906 may take into account one or more interstitual glucose level readings. For example, medication dosing unit 1906 may take into account the most recent reading. Medication dosing unit 1906 may calculate certain parameters that are indicative of changes in interstitual glucose level readings. For example, medication dosing unit 1906 may calculate the minimum, mean, maximum, standard deviation, slope or second derivative of interstitual glucose level readings over one or more time windows. A time window may span a period of time preceding the transition to the meal-in-progress state, span a period of time that includes the transition to the meal-in-progress state, or span a period of time some time after the transition to the meal-in-progress state. Other or additional measurement sensor units such as heart rate, blood pressure, body temperature, hydration level, fatigue level are also possible. An insulin delivery system may also take into account a user's current location.

Medication dosing unit 1906 may also take into account other inputs such as information related to a user's current or recent physical activity, sleep, stress etc. Medication dosing unit 1906 may also take into account personal information such as gender, age, height, weight, etc.

Medication dosing unit 1906 may also take into account information related to a user's medication dosing needs, such as for example a user's insulin basal rates, a user's insulin-to-carb ratios, and a user's insulin correction factor. This information may be entered or configured by the user, by a caregiver or by a health record or healthcare maintenance system. Information related to a user's medication dosing needs may also be derived from historical data collected and stored by the medication dispensing system. For example, the dosage of medication (e.g. insulin) delivered by the medication dispensing unit in a period of time preceding the current food intake event. Medication dosing unit 1906 may take into account medication dosages delivered in connection with one or more prior food intake events that occurred in the past at or around (e.g., within a specified time window) the same time of day, and/or the same day of the week.

Medication dosing unit 1906 may also take into account the medication still active from previous medication dispensing events, such as for example the insulin-on-board.

Medication dosing unit 1906 may also include parameters related to food intake events that occurred in the past at or around (e.g. within a specified time window) the same time of day, and/or the same day of the week, and/or at the same location. Medication dosing system 1906 may for example look at the duration of past food intake events, the estimated amounts consumed during past food intake events, the average pace of eating during past food intake events, the eating methods of past food intake events, the type of utensils or containers used during past food intake events, or the amounts of carbohydrates consumed during past food intake events. Other parameters are also possible. Some of these additional parameters (e.g., duration or pace) may be computed by the food intake tracking and feedback system without requiring any user intervention. In other cases, a user intervention, input or confirmation by the user may be necessary.

Medication Dispensing Schedule

Medication dosing unit 1906 may instruct medication dispensing unit to administer the initial medication dosage all at once, or may specify a delivery schedule for administering the medication. In one embodiment of the current disclosure, medication dosing unit 1906 computes the medication dosage as well as a schedule for the delivery of the medication. As an example, medication dosing unit 1906 may determine that 5 units of insulin need to be delivered and may specify a delivery schedule as follows: 2 units to be administered immediately, 1 unit after 2 minutes, 1 unit after 5 minutes and 1 unit after 7 minutes. This is just one example and other time profile structures are of course possible.

Medication dosing unit 1906 may communicate both the medication dosage and schedule to medication dispensing unit 1908. Alternatively, medication dosing unit 1906 may manage the schedule and send one or more messages to medication dispensing unit 1908 every time medication needs to be administered along with the dosage of medication to be administered.

In a preferred embodiment of the current disclosure, medication dosing unit 1906 may upon entering the meal-in-progress state or some time thereafter instruct 1907 medication dispensing unit 1908 to initiate delivery of medication. It may for example instruct medication dispensing unit 1908 to deliver one or more small micro-doses of medication.

Additional Dosages and Dosage Adjustments

During the food intake event and/or some time after the food intake event, medication dosing unit 1906 may periodically (e.g., every couple of minutes) or continuously monitor in part one or more inputs 1905 from measurement sensor processing unit(s) 1909, and/or one or more inputs 1903 from dietary tracking and feedback system 1902 to determine if and how much additional medication should be administered or whether a scheduled medication dispensing should be adjusted. Other inputs such as inputs described in earlier sections of this disclosure may also be taken into account.

When computing a medication dosage or medication dosage adjustment, medication dosing unit 1906 may take into account whether or not a food intake event is in progress. If a food intake event is not or no longer in progress, medication dosing unit 1906 may for example take into account the time since the end of the last food intake event. If a food intake event is in progress, medication dosing unit 1906 may for example take into account the time elapsed since the start of the current food intake event, the average or median pace of eating since the start of the current food intake event, the estimated total amounts consumed since the start of the current food intake event. Other examples are also possible.

Medication dosing unit 1906 may also take into account one or more recent inputs from measurement sensor processing unit 1909. For example, in case medication dosing unit 1906 is an insulin dosing unit in an automated insulin delivery system (aka artificial pancreas) and measurement sensor unit 1909 is a CGM, medication dosing unit 1906 may take into account the value of the most recent interstitial glucose level reading and/or the change in interstitial glucose level readings over a time window immediately or closely preceding the current time. If the most recent interstitial glucose level reading is below a specified threshold and/or a change in interstitial glucose level readings is exceeding a specified negative threshold, medication dosing unit 1906 may determine to adjust the insulin dosage down, or suspend insulin delivery until the interstitial glucose level readings reaches a second specified threshold and/or the change in interstitial glucose level readings is no longer exceeding a second specified negative threshold, has turned positive or is exceeding a specified positive threshold.

In some embodiments of the current disclosure, upon detecting of a concerning measurement sensor processing unit output, medication dosing unit 1906 may send an alert to the user, one or more of his caregivers, a healthcare provider, a monitoring system or to an emergency response system, or to a third party who may have a direct or indirect interest in being informed about the occurrence of such episodes.

Likewise, if the most recent interstitial glucose level reading exceeds a specific threshold and/or a change in interstitial glucose level readings is exceeding a specified positive threshold, medication dosing unit 1906 may determine that an additional medication dosage should be administered, that an already scheduled medication dosage needs to be adjusted to a larger dosage or delivered at a time earlier than the currently scheduled time. Medication dosing unit 1906 may optionally take into account additional inputs from dietary tracking and feedback system 1902 to compute the additional medication dosage or medication dosage adjustment. Medication dosing unit 1906 may send one or more messages 1907 to medication dispensing unit 1908 to inform medication dispensing unit 1908 of the additional or adjusted medication dispensing requirements.

Upon detection of an actual or imminent end of a food intake event, or some time thereafter, dietary tracking and feedback system 1902 may send a signal 1903 to medication dosing unit 1906 to inform medication dosing unit 1906 that an actual or imminent end of a food intake event has been detected. Medication dosing unit 1906 may use this information to change its state to a "no-meal-in-progress" state. In specific embodiments, the medication dosing unit, when in a no-meal-in-progress state may periodically or continuously monitor in part one or more inputs 1905 from measurement sensor processing unit(s) 1909, and/or one or more inputs 1903 from dietary tracking and feedback system 1902 to determine if and how much additional medication should be administered or whether a scheduled medication dispensing should be adjusted. Other inputs such as inputs described in earlier sections of this disclosure may also be taken into account. When in the no-meal-in-progress state, the frequency of monitoring and/or updating/adjusting medication dosing may be different from the frequency of monitoring and/or updating/adjusting medication dosing when in the "meal-in-progress" state. The algorithms used to determine a medication dosage or medication dosage adjustment may also be different between the "meal-in-progress" state and the "no-meal-in-progress" state.

Description of Medication Dosing Learning System

In some embodiments of the current disclosure, medication dosing unit 1906 may collect, and store data and information about food intake events. In some embodiments, medication dosing unit 1906 may perform additional processing steps on collected data and information before storing. Processing steps may be filtering, averaging, applying arithmetical operations, and applying statistical operations. Other processing steps are also possible.

Data and information about food intake events might be stored as data elements in a database that maintains data records about food intake events.

Data elements may be event data elements and contain information or parameters that characterize the food intake event. Such information may include, but is not limited to, the event start time, the day of week the event occurred, the date of the event, the duration of the event, the event end time, metrics associated with the speed or pace at which subject is eating or drinking, metrics associated with the amounts of food or liquid consumed during the event.

Data elements may also be measurement data elements and contain information or parameters that characterize one or more signals measured by one or more measurement sensor units 1904 and processed by one or more measurement sensor processing units 1909. Such information may include, but is not limited to, sensor reading levels corresponding to specific times in connection with the food intake event, or the average, minimum, or maximum sensor reading levels corresponding to specific time windows in connection with the food intake event. Specific times might for example be the start of the food intake event, periodic or pre-defined points in time during the food intake event, the end of the food intake event, or periodic or pre-defined times after the food intake event. Other times are also possible. Specific time windows might for example be a duration of time immediately preceding the start of the food intake event, a duration of time prior to the start of the food intake event, the duration of the food intake event, a specific duration of time within the food intake event, a duration of time immediately following the end of a food intake event or a duration of time some time after the end of a food intake event.

In one specific embodiment the medication dosing unit is an automated insulin delivery system, and the sensor reading levels are interstitial glucose reading levels obtained from a continuous glucose monitoring sensor.

Data elements may also be dosage data elements and contain information or parameters that characterize the medication dosage and delivery schedule in connection with the food intake event.

Other data elements are also possible. One or more event data elements, one or more measurement data elements and/or one or more dosage data elements of the same food intake event may be recorded as a single record entry in a database. Event data elements, measurement data elements and/or dosage data elements may also be recorded as separate records in a database. Other data structures consistent with the teachings herein might also be used, or used instead.

Medication dosing unit 1906 may include a processing and analysis subsystem.

The processing and analysis subsystem may use statistics, machine learning or artificial intelligence techniques on entries in the database to build a model that recommends an adequate medication dosage and/or delivery schedule. The processing and analysis subsystem may be used to recommend an initial medication dosage, and/or to recommend additional medication dosage(s) or dosage adjustment(s).

Figure 9:
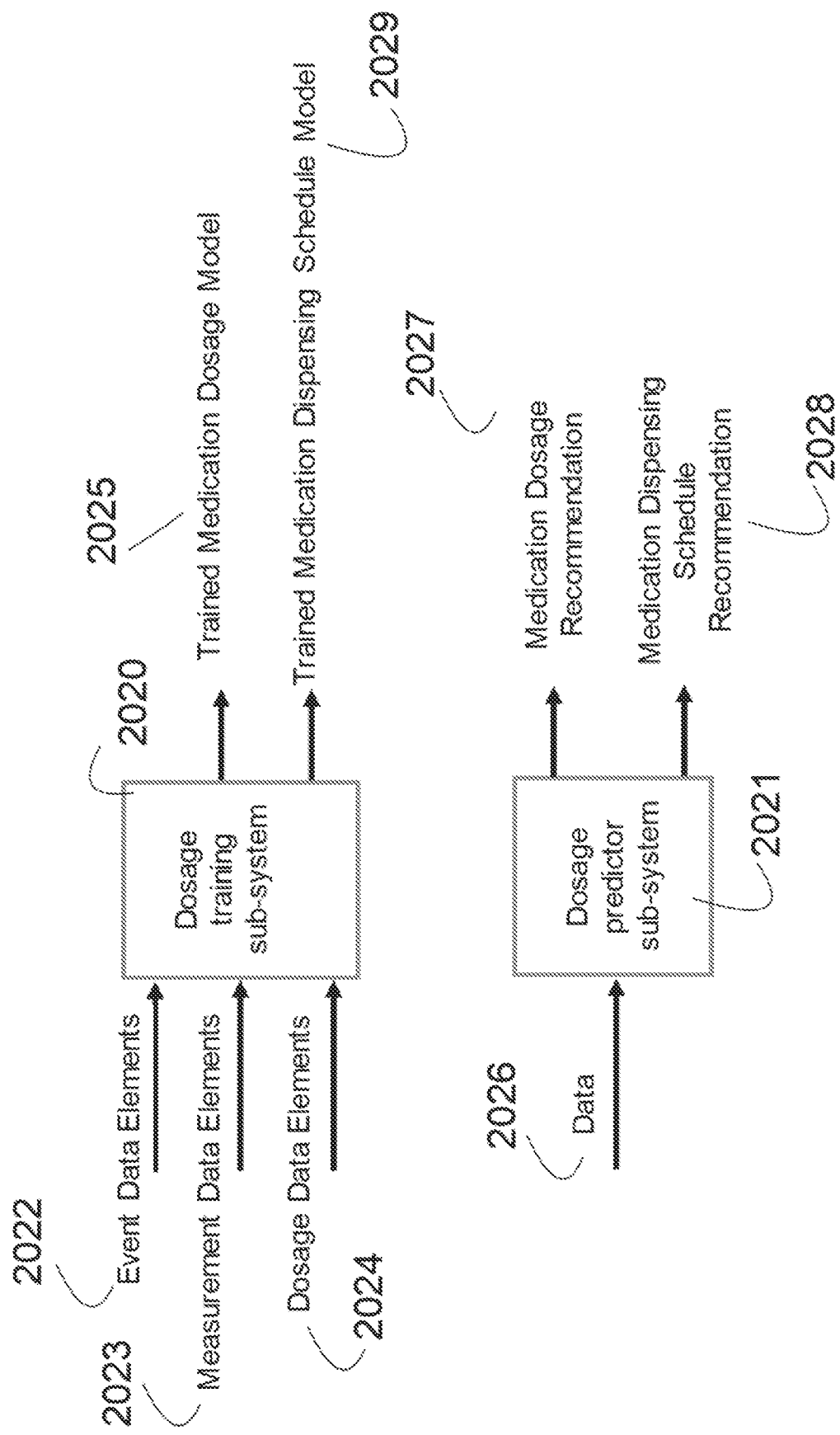
FIG. 9 is an illustrative example of a machine learning system that might be used with other elements described in this disclosure.

FIG. 9 is an illustrative example of a machine learning system that might be used with other elements described in this disclosure. The machine learning system of FIG. 9 includes a dosage training subsystem 2020 and a dosage predictor subsystem 2021. In some embodiments of the present disclosure, the machine learning system may include additional subsystems or modified versions of the subsystems shown in FIG. 2. Dosage training subsystem 2020 might use event data elements 2022, measurement data elements 2023 and dosage data elements 2024 as inputs. The dosage training sub-system applies machine learning techniques to build a model that recommends an adequate medication dosage and/or a medication dispensing schedule. It might use supervised learning techniques on one or more entries from the database to train the model. Event data element(s) 2022 and/or measurement data element(s) 2023 might be used as features for the model. One or more dosage data elements 2024 might be used as labels. Trained model(s) 2025 and/or 2029 is then used in dosage predictor subsystem 2021 to generate a medication dosage recommendation and/or medication dispensing recommendation corresponding to a new unlabeled data input 2026.

Medication dosing unit 1906 may include a processing unit and perform additional processing on the data elements and analyze the data to extract information about the user's eating and drinking activities and behaviors, sensor measurements (e.g., glycemic control) and/or medication regimen. Processing may include but is not limited to filtering, extracting specific data elements, modifying data or data elements, combining data or data elements. Analysis may also include comparing specific data elements to data that is stored in a look up table or database, correlating data elements to data elements that were obtained at an earlier time and/or from different subjects. Medication dosing unit 1906 may store raw or processed data in one or more data storage unit(s). Storage may be temporary or permanent.

In some variations, records in the database may be subdivided into groups (e.g., based on meal type—breakfast, lunch, dinner, snack) and a different model may be used for each subgroup. Alternatively, the same model may be used but it may be trained using data from only one or a selective set of subgroups. In other variations, instead of a supervised machine learning approach (i.e., where features are specified manually), unsupervised learning may be used instead. With unsupervised learning, the classifier will autonomously generate features from the raw dataset provided.

Medication dosing unit 1906 may collect, and store data and information about other user activities. For example, medication dosing unit 1906 may collect information or data about a user's physical activity, sleep activity, sexual activity. Medication dosing unit 1906 may also collect and store information about a user's stress, heart rate, blood pressure etc. In some embodiments, medication dosing unit 1906 may perform additional processing steps on collected data and information before storing. Processing steps may be filtering, averaging, applying arithmetical operations, and applying statistical operations. Other processing steps are also possible. Medication dosing unit 1906 may link this data and information to one or more food intake events. Data and information about food intake events might be stored as data elements in a database that maintains data records about food intake events. These data elements may also be used as inputs to processing and analysis subsystem of medication dosing unit 1906. For example, these data elements may be used as additional or alternative event data inputs to dosage training subsystem 1920. These data elements may for example be features for the model.

Medication dosing system 1906 may also collect inputs such as information related to a user's physical activity, sleep, stress etc. Medication dosing system 1906 may for example compare a user's current or recent physical activity to past physical activity and use the output of that comparison into the calculation of a medication dosage.

While not illustrated in detail in FIG. 9, the machine learning system, dosage training subsystem 2020, and dosage predictor subsystem 2021 can be implemented using various structural elements. For example, dosage prediction might be implemented using computer hardware, such as a processor, program code memory and program code stored in the program code memory. This might be a separate embedded unit, or might be implemented on a processor with memory that is used for other functions and tasks as well as dosage prediction. This processor and memory might be built into a wearable device, a mobile device that communicates with a wearable device, a server that is in communication, directly or indirectly, with a wearable device or sensors, or some combination of the above. Other elements might similarly be implemented, such as storage for event data elements 2022, storage for measurement data elements 2023 and storage for dosage data elements 2024, program code that implements the machine learning techniques to build a model that recommends an adequate medication dosage and/or a medication dispensing schedule, storage for the model, storage for a database to train the model, and hardware circuitry needed to communicate messages, such as sending a medication dosage recommendation message, a medication dispensing recommendation message, or a signal to a hardware device that dispenses medication.

In certain embodiments, the medication dispensing system of FIG. 8 may operate without any manual intervention or at least not requiring any manual intervention. In other embodiments, the medication dispensing system of FIG. 8 may require some manual intervention. In one example, medication dosing unit 1906 may calculate a medication dosage and/or medication delivery schedule but, instead of instructing the medication dispensing unit 1908 to initiate or schedule delivery of medication, it may send a message to the patient, one or more caregivers of the patient, a healthcare professional, a monitoring system, etc. to confirm the proposed medication dosage and/or medication delivery schedule. The message can be a text message, a push notification, a voice message, etc., but other message formats are also possible.

In some embodiments, the patient, caregiver, etc. may have an option to alter the proposed medication dosage and/or medication delivery schedule. Upon receiving a confirmation from the patient, caregiver, etc., medication dosing unit 1906 may send one or more instructions to the medication dispensing unit 1908 to initiate or schedule delivery of medication. The instruction(s) may also be sent by a device or unit other than the medication dosing unit 1906. As an example, the instruction(s) may be sent to the medication dispensing unit 1908 directly from the device on which the patient, caregiver etc. received the message to confirm the medication dosage and/or medication delivery schedule. Other user interventions are also possible, such as allowing for a "snooze" function to move a message to a predetermined time in the future.

Interpretation

Conjunctive language, such as phrases of the form "at least one of A, B, and C," or "at least one of A, B and C," unless specifically stated otherwise or otherwise clearly contradicted by context, is otherwise understood with the context as used in general to present that an item, term, etc., may be either A or B or C, or any nonempty subset of the set of A and B and C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Further embodiments can be envisioned to one of ordinary skill in the art after reading this disclosure. In other embodiments, combinations or sub-combinations of the above-disclosed invention can be advantageously made. The example arrangements of components are shown for purposes of illustration and it should be understood that combinations, additions, re-arrangements, and the like are contemplated in alternative embodiments of the present invention. Thus, while the invention has been described with respect to exemplary embodiments, one skilled in the art will recognize that numerous modifications are possible.

For example, the processes described herein may be implemented using hardware components, software components, and/or any combination thereof. The specification and drawings are, accordingly, to be regarded in an illustrative rather than a restrictive sense. It will, however, be evident that various modifications and changes may be made thereunto without departing from the broader spirit and scope of the invention as set forth in the claims and that the invention is intended to cover all modifications and equivalents within the scope of the following claims.

All references, including publications, patent applications, and patents, cited herein are hereby incorporated by reference to the same extent as if each reference were individually and specifically indicated to be incorporated by reference and were set forth in its entirety herein.

What is claimed is:

1. A system comprising:
    one or more processors; and
    one or more processor-readable media storing instructions which, when executed by the one or more processors, cause performance of:
        obtaining gesture detection data corresponding to consumption of a food item or a drink;
        determining, based on the gesture detection data, nutritional content of the food item or the drink by comparing the gesture detection data to historical consumption data that includes historical gesture detection data and associated nutritional content information of one or more food items or drinks; and
        causing delivery of insulin in accordance with the nutritional content of the food item or the drink.

2. The system of claim 1, wherein the gesture detection data comprises consumption mode data indicating which utensils or equipment were used during consumption of the food item or the drink.

3. The system of claim 1, wherein the gesture detection data comprises consumption mode data indicating that utensils were not used during consumption of the food item.

4. The system of claim 1, wherein the gesture detection data comprises pace metrics for consumption of the food item or the drink.

5. The system of claim 1, wherein the gesture detection data comprises duration information for consumption of the food item or the drink.

6. The system of claim 1, wherein the one or more processor-readable media further store instructions which, when executed by the one or more processors, cause performance of:
    obtaining location information corresponding to consumption of the food item or the drink.

7. The system of claim 1, wherein the one or more processor-readable media further store instructions which, when executed by the one or more processors, cause performance of:
    obtaining time of event information corresponding to consumption of the food item or the drink.

8. The system of claim 1, wherein the associated nutritional content information of the one or more food items or drinks includes food/drink identification data and quantity information.

9. The system of claim 1, wherein causing delivery of insulin in accordance with the nutritional content of the food item or the drink comprises:
    generating, based on the nutritional content, an insulin dosage recommendation; and
    communicating the insulin dosage recommendation to a user.

10. The system of claim 1, wherein causing delivery of insulin in accordance with the nutritional content of the food item or the drink comprises:
    interacting with an insulin delivery device to administer an insulin dosage without user intervention.

11. A processor-implemented method comprising:
    obtaining gesture detection data corresponding to consumption of a food item or a drink;
    determining, based on the gesture detection data, nutritional content of the food item or the drink by comparing the gesture detection data to historical consumption data that includes historical gesture detection data and associated nutritional content information of one or more food items or drinks; and causing delivery of insulin in accordance with the nutritional content of the food item or the drink.

12. The method of claim 11, wherein the gesture detection data comprises consumption mode data indicating which utensils or equipment were used during consumption of the food item or the drink.

13. The method of claim 11, wherein the gesture detection data comprises consumption mode data indicating that utensils were not used during consumption of the food item.

14. The method of claim 11, wherein the gesture detection data comprises pace metrics for consumption of the food item or the drink.

15. The method of claim 11, wherein the gesture detection data comprises duration information for consumption of the food item or the drink.

16. The method of claim 11, further comprising:
obtaining location information corresponding to consumption of the food item or the drink.

17. The method of claim 11, further comprising:
obtaining time of event information corresponding to consumption of the food item or the drink.

18. The method of claim 11, wherein the associated nutritional content information of the one or more food items or drinks includes food/drink identification data and quantity information.

19. The method of claim 11, wherein causing delivery of insulin in accordance with the nutritional content of the food item or the drink comprises:

generating, based on the nutritional content, an insulin dosage recommendation; and communicating the insulin dosage recommendation to a user.

20. One or more non-transitory processor-readable media storing instructions which, when executed by one or more processors, cause performance of:

obtaining gesture detection data corresponding to consumption of a food item or a drink;

determining, based on the gesture detection data, nutritional content of the food item or the drink by comparing the gesture detection data to historical consumption data that includes historical gesture detection data and associated nutritional content information of one or more food items or drinks; and causing delivery of insulin in accordance with the nutritional content of the food item or the drink.

* * * * *